US011780901B2

(12) United States Patent
Gellman et al.

(10) Patent No.: US 11,780,901 B2
(45) Date of Patent: *Oct. 10, 2023

(54) ANALOGUES OF PARATHYROID HORMONE (1-34) THAT FUNCTION AS AGONISTS OF THE PARATHYROID HORMONE RECEPTOR-1 AND DISPLAY MODIFIED ACTIVITY PROFILES

(71) Applicant: Wisconsin Alumni Research Foundation, Madison, WI (US)

(72) Inventors: Samuel H. Gellman, Madison, WI (US); Shi Liu, Madison, WI (US); Thomas J. Gardella, Needham, MA (US)

(73) Assignees: Wisconsin Alumni Research Foundation, Madison, WI (US); The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/031,178

(22) Filed: Sep. 24, 2020

(65) Prior Publication Data

US 2021/0155666 A1 May 27, 2021

Related U.S. Application Data

(63) Continuation of application No. 16/109,114, filed on Aug. 22, 2018, now abandoned, which is a continuation-in-part of application No. 14/312,012, filed on Jun. 23, 2014, now Pat. No. 10,501,518.

(60) Provisional application No. 61/940,124, filed on Feb. 14, 2014, provisional application No. 61/838,307, filed on Jun. 23, 2013, provisional application No. 62/548,442, filed on Aug. 22, 2017.

(51) Int. Cl.
*C07K 14/635* (2006.01)
*A61K 38/00* (2006.01)

(52) U.S. Cl.
CPC ............ *C07K 14/635* (2013.01); *A61K 38/00* (2013.01)

(58) Field of Classification Search
CPC ............................. C07K 14/635; A61K 38/00
See application file for complete search history.

(56) References Cited

U.S. PATENT DOCUMENTS

| 5,393,869 A | 2/1995 | Nakagawa et al. |
| 5,434,246 A | 7/1995 | Fukuda et al. |
| 5,556,940 A | 9/1996 | Willick et al. |
| 5,589,452 A | 12/1996 | Krstenansky et al. |
| 5,717,062 A | 2/1998 | Chorev et al. |
| 2002/0061838 A1 | 5/2002 | Holmquist et al. |
| 2002/0160945 A1 | 10/2002 | Cantor |
| 2003/0039654 A1* | 2/2003 | Kostenuik ............ A61P 5/14 514/16.7 |
| 2005/0033023 A1 | 2/2005 | Correale et al. |
| 2005/0124537 A1 | 6/2005 | Kostenuik et al. |
| 2005/0261183 A1 | 11/2005 | Stewart et al. |
| 2008/0058505 A1* | 3/2008 | Gardella ............... A61P 19/08 530/399 |
| 2008/0108562 A1* | 5/2008 | Riviere ................. A61K 38/29 514/16.7 |
| 2010/0150909 A1 | 6/2010 | Stewart et al. |
| 2010/0256060 A1 | 10/2010 | Stern |
| 2012/0083448 A1 | 4/2012 | Xu et al. |
| 2014/0315791 A1 | 10/2014 | Horne et al. |
| 2014/0378382 A1 | 12/2014 | Gellman et al. |
| 2015/0175664 A1 | 6/2015 | Karim et al. |

OTHER PUBLICATIONS

Caporale et al., 2009, Structure-function relationship studies of PTH(1-11) analogues containing D-amino acids, European Journal of Pharmacology, 611: 1-7.*
Peggion et al., 2002, Structure-Function Studies of Analogues of Parathyroid Hormone (PTH)-1-34 Containing beta-Amino Acid Residues in Positions 11-13, Biochemistry, 41: 8162-8175.*
Hook et al., 2005, The Proteolytic Stability of "Designed" beta-Peptides Containing alpha-Peptide-Bond Mimics and of Mixed alpha, beta-Peptides: Application to the Construction of MHC-Binding Peptides, Chemistry & Biodiversity, 2: 591-632.*
Aguilar et al., 2007, beta-Amino acid-containing hybrid peptides-new opportunities in peptidomimetics, Organic & Biomolecular Chemistry, 5: 2884-2890.*
Steer et al., 2002, Beta-Amino Acids: Versatile Peptidomimetics, Current Medicinal Chemistry, 9: 811-822.*
Seebach et al., 2004, The World of beta-and gamma-Peptides Comprised of Homologated Proteinogenic Amino Acids and other Compounds, Chemistry & Biodiversity, 1: 1111-1239.*
Cabrele et al., 2014, Peptides Containing beta-Amino Acid Patterns: Challenges and Successes in Medicinal Chemistry, Journal of Medicinal Chemistry, 57: 9718-9739.*
Frackenpohl et al., 2001, The Outstanding Biological Stability of beta- and gamma-Peptides toward Proteolytic Enzymes: An In Vitro Investigation with Fifteen Peptidases, ChemBioChem, 2: 445-455.*
Gentilucci et al., 2010, Chemical Modification Designed to Improve Peptide Stability: Incorporation of Non-Natural Amino Acids, Pseudo-Peptide Bonds, and Cyclization, Current Pharmaceutical Design, 16: 3185-3203.*
Bergwitz, et al., Residues in the membrane-spanning and extracellular loop regions of the parathyroid hormone (PTH)-2 receptor determine signaling selectivity for PTH and PTH-related peptide. *Journal of Biological Chemistry* 272, 28861-28868 (1997).
Berlot, C.H. A highly effective dominant negative $\alpha_s$ construct containing mutation: that affect distinct functions inhibits multiple $G_s$-coupled receptor signaling pathways. *J Biol. Chem.* 277, 21080-21085 (2002).

(Continued)

*Primary Examiner* — Amber D Steele
(74) *Attorney, Agent, or Firm* — Joseph T. Leone; DeWitt LLP

(57) ABSTRACT

Described are polypeptide analogs of parathyroid hormone (PTH) that include an unnatural amino acid substitution at positions 7 or 8 from the N-terminus of the polypeptide. Also described are pharmaceutical compositions useful for treating hypoparathyroidism that contain the analogs and methods of using the analogs to treat hypoparathyroidism.

20 Claims, 12 Drawing Sheets

Specification includes a Sequence Listing.

(56) References Cited

OTHER PUBLICATIONS

Bilezikian et al., 2016, Management of Hypoparathyroidism : Present and Future, *J. Clin. Endocrinol. Metab.*, 101(6): 2313-2324.
Binkowski, B.F. et al. A Luminescent Biosensor with Increased Dynamic Range for Intracellular cAMP. *ACS Chem. Biol.* 6, 1193-1197 (2011).
Boersma, M.D. et al. Evaluation of Diverse alpha/beta-Backbone Patterns fo Functional α-Helix Mimicry: Analogs of the Bim BH3 Domain. *J. Am. Chem. Soc.* 134, 315-323 (2012).
Dean, T. et al. Mechanisms of ligand binding to the parathyroid hormone (PTH)/PTH-related protein receptor: Selectivity of a modified PTH(1-15) Radioligand for G$\alpha_s$-coupled receptor conformations. *Mol. Endocrinol.* 20, 931-943 (2006).
Dean, T. et al. Altered selectivity of parathyroid hormone (PTH) and PTH-Related protein (PTHrP) for distinct conformations of the PTH/PTHrP receptor. *Mol. Endocrinol.* 22, 156-166 (2008).
Feinstein, T.N. et al. Retromer terminates the generation of cAMP by internalized PTH receptors. *Nat. Chem. Biol.* 7, 278-284 (2011).
Feng et al., 2016, Inspiration from the mirror: D-Amino acid containing peptides in biomedical approaches, *Biomol. Concepts*, 7(3):179-187.
Gardella, T. J. et al. Analysis of Parathyroid Hormone's Principal Receptor-binding Region by Site-directed Mutagenesis and Analog, *Endocrinology* 132, 2024-2030 (1993).
Gardella, T.J. et al. Converting parathyroid hormone-related peptide (PTHrP) into a potent PTH-2 receptor agonist. *Journal of Biological Chemistry* 271, 19888-19893 (1996).
Gill, S.C. et al. Calculation of protein extinction coefficients from amino-acid sequence data. *Analytical Biochemistry* 182, 319-326 (1989).
Hoare, S.R.J. et al. Measurement of agonist and antagonist ligand-binding parameters at the human parathyroid hormone type 1 receptor: Evaluation of receptor states and modulation by guanine nucleotide. *J. Pharmacol. Exp. Ther.* 289, 1323-1333 (1999).
Hoare, S.R.J. et al. Molecular determinants of tuberoinfundibular peptide of 39 residues (TIP39) selectivity for the parathyroid hormone-2 (PTH2) receptor-N-terminal truncation of TIP39 reverses PTH2 receptor/PTH1 receptor binding selectivity. *Journal of Biological Chemistry* 275, 27274-27283 (2000).
Hoare, S.R.J. et al. Evaluating the signal transduction mechanism of the parathyroid hormone 1 receptor—Effect of receptor-G-protein interaction on the ligand binding mechanism and receptor conformation. *J. Biol. Chem.* 276, 7741-7753 (2001).
Horne, W.S et al. Sequence-based design of α/β-peptide foldamers that mimic BH3 domains. *Angew. Chem. Int. Ed.* 47, 2853-2856 (2008).
Horne, W.S. et al. Structural and biological mimicry of protein surface recognition by α/β-peptide foldamers. *Proc. Natl. Acad. Sci. U.S.A.* 106, 14751-14756 (2009).
Irannejad et al. "Functional selectivity of GPCR-directed drug action through location bias," *Nature Chemical Biology* 13:799-806 (2017).
Kenakin, T. et al. Signaling bias in new drug discovery: detection, quantification and therapeutic impact. *Nat. Rev. Drug Discovery* 12, 205 (2013).
King, D. S. et al. A cleavage method which minimizes side reactions following FMOC solid-phase peptide-synthesis, *International Journal of Peptide and Protein Research* 36, 255-266 (1990).
Kostenuik, P.J. et al. Infrequent delivery of a long-acting PTH-FC fusion protein has potent anabolic effects on cortical and cancellous bone. *Journal of Bone and Mineral Research* 22, 1534-1547 (2007).
Koth, C.M. et al. Molecular basis for negative regulation of the glucagon receptor. *Proc. Natl. Acad. Sci. U.S.A.* 109, 14393-14398 (2012).
Lagerstrom, M.C. et al. Structural diversity of G protein-coupled receptors and significance for drug discovery. *Nat. Rev. Drug Discovery* 7, 339-357 (2008).
Maeda, A., et al. Critical role of parathyroid hormone (PTH) receptor-1 phosphorylation in regulating acute responses to PTH. *Proc. Natl. Acad. Sci. U.S.A.* 110, 5864-5869 (2013).
Neer, R.M. et al. Effect of parathyroid hormone (1-34) on fractures and bone mineral density in postmenopausal women with osteoporosis. *N. Engl. J. Med.* 344, 1434-1441 (2001).
Okazaki, M. et al. Prolonged signaling at the parathyroid hormone receptor by peptide ligands targeted to a specific receptor conformation. *Proc. Natl. Acad. Sci. U.S.A.* 105, 16525-16530 (2008).
Pal, K.. et al. Structure and mechanism for recognition of peptide hormones by Class B G-protein-coupled receptors. *Acta Pharmacol. Sin.* 33, 300-311 (2012).
Parthier, C. et al. Passing the baton in class B GPCRs: peptide hormone activation via helix induction? *Trends Biochem. Sci.* 34, 303-310 (2009).
Pioszak, A.A. et al. Molecular recognition of parathyroid hormone by its G protein-coupled receptor. *Proc. Natl. Acad. Sci. U.S.A.* 105, 5034-5039 (2008).
Piserchio, A. et al. Residue 19 of the parathyroid hormone: Structural consequences. *Biochemistry* 41, 13217-13223 (2002).
Qin, L. et al.. Parathyroid hormone: a double-edged sword for bone metabolism. *Trends in Endocrinology and Metabolism* 15, 60-65 (2004).
Rajagopal, S. et al. Teaching old receptors new tricks: biasing seven- transmembrane receptors. *Nat. Rev. Drug Discovery* 9, 373-386 (2010).
Rajagopal, S. et al. Quantifying Ligand Bias at Seven-Transmembrane Receptors. *Mol. Pharmacol.* 80, 367-377 (2011).
Rasmussen, S.G.F. et al. Crystal structure of the $\beta_2$ adrenergic receptor-Gs protein complex. *Nature* 477, 549-U311 (2011).
Schievano, E. et al. Conformational and biological characterization of human parathyroid hormone hPTH(1-34) analogs containing beta-amino acid residues in positions 17-19. *Biopolymers* 70, 534-547 (2003).
Serada, M. et al. The role of the liver and kidneys in the pharmacokinetics of subcutaneously administered teriparatide acetate in rats. *Xenobiotica* 42, 398-407 (2012).
Shimizu, M. et al. Minimization of parathyroid hormone—Novel amino-terminal parathyroid hormone fragments with enhanced potency in activating the type-1 parathyroid hormone receptor. *J. Biol. Chem.* 275, 21836-21843 (2000).
Shimuzu et al. "Pharmacodynamic Actions of a Long-Acting PTH Analog (LA-PTH) in Thyroparathyroidectomized (TPTX) Rats and Normal Monkeys," *J Bone Miner Res.* 31 (7):1405-12 (2016).
Uzawa, T., et al. Comparison of the Effects of Intermittent and Continuous Administration of Human Parathyroid Hormone(1-34) on Rat Bone. *Bone* 16, 477-484 (1995).
Venkatakrishnan, A.J. et al. Molecular signatures of G-protein-coupled receptors. *Nature* 494, 185-194 (2013).
Vilardaga, J.P. et al. Molecular basis of parathyroid hormone receptor signaling and trafficking: a family B GPCR paradigm. *Cell. Mol. Life Sci.* 68, 1-13 (2011).

\* cited by examiner

| | (R*)-β²AA | (S*)-β²AA | (S*)-β³AA | (D)-AA |
|---|---|---|---|---|
| 1 | ■ | ■ | | |
| 2 | | | ■ | |
| 3 | | | | |
| 4 | | | | |
| 5 | | | ■ | |
| 6 | | | ■ | |
| 7 | ■ | | ■ | ■ |
| 8 | ■ | | ■ | |

Green color denotes good tolerance of β-AA or D-AA for cAMP activation

```
PTH:       SVSEIQLMHNLGKHLNSMERVEWLRKKLQDVHNF  (SEQ. ID. NO: 14)
Ligand 1:  SVSEIQLMHNLGKHLNSMERVEWLRKKLQDVHNF  (SEQ. ID. NO: 1)
Ligand 2:  SVSEIQLMHNLGKHLNSMERVEWLRKKLQDVHNF  (SEQ. ID. NO: 2)
Ligand 3:  SVSEIQLMHNLGKHLNSMERVEWLRKKLQDVHNF  (SEQ. ID. NO: 3)
Ligand 4:  SVSEIQLMHNLGKHLNSMERVEWLRKKLQDVHNF  (SEQ. ID. NO: 4)
Ligand 5:  SVSEIQLMHNLGKHLNSMERVEWLRKKLQDVHNF  (SEQ. ID. NO: 5)
Ligand 6:  SVSEIQLMHNLGKHLNSMERVEWLRKKLQDVHNF  (SEQ. ID. NO: 6)
Ligand 7:  SVSEIQLMHNLGKHLNSMERVEWLRKKLQDVHNF  (SEQ. ID. NO: 7)
Ligand 8:  SVSEIQLMHNLGKHLNSMERVEWLRKKLQDVHNF  (SEQ. ID. NO: 8)
Ligand 9:  SVSEIQLMHNLGKHLNSMERVEWLRKKLQDVHNF  (SEQ. ID. NO: 9)
Ligand 10: SVSEIQLMHNLGKHLNSMERVEWLRKKLQDVHNF  (SEQ. ID. NO: 10)
Ligand 11: SVSEIQLLHNLGKHLNSMERVEWLRKKLQDVHNF  (SEQ. ID. NO: 11)
Ligand 12: SVSEIQLLHNLGKHLNSMERVEWLRKKLQDVHNF  (SEQ. ID. NO: 12)
Ligand 13: SVSEIQLHNLGKHLNSMERVEWLRKKLQDVHNF   (SEQ. ID. NO: 13)
```

Red: (R*)-β²AA        (S*)-β²AA
Blue: (S*)-β³AA       (D)-AA

FIG. 4

SEQUENCE LISTING

<160> NUMBER OF SEQ ID NOS: 45

<210> SEQ ID NO 1
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:

```
<221> NAME/KEY: MOD_RES
<222> LOCATION: (1)..(1)
<223> OTHER INFORMATION: S at position 1 is (R*) Beta-2 Serine

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 2
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (1)..(1)
<223> OTHER INFORMATION: S at position 1 is (S*) Beta=2 Serine

<400> SEQUENCE: 2

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 3
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (1)..(1)
<223> OTHER INFORMATION: S at position 1 is (S*) Beta-3 Serine

<400> SEQUENCE: 3

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 4
<211> LENGTH: 34
<212> TYPE: PRT
<213> ORGANISM: Artificial Sequence
<220> FEATURE:
<223> OTHER INFORMATION: Synthetic polypeptide.
<220> FEATURE:
<221> NAME/KEY: MOD_RES
<222> LOCATION: (1)..(1)
<223> OTHER INFORMATION: S at position 1 is (D)-Serine.

<400> SEQUENCE: 4

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe
```

```
<210> SEQ ID NO 5
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (2)..(2)
<223> OTHER INFORMATION: V at position 2 is (S*) Beta-3 Valine.

<400> SEQUENCE: 5

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 6
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (5)..(5)
<223> OTHER INFORMATION: I at position 5 is (S*) Beta-2 isoleucine

<400> SEQUENCE: 6

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 7
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (6)..(6)
<223> OTHER INFORMATION: Q at position 6 is (S*) Beta-2 Glutamine.

<400> SEQUENCE: 7

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 8
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (7)..(7)
<223> OTHER INFORMATION: L at position 7 is (R*) Beta-2 Leucine.
```

-continued

```
<400> SEQUENCE: 8

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 9
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (7)..(7)
<223> OTHER INFORMATION: L at position 7 is (S*) Beta-2 Leucine

<400> SEQUENCE: 9

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 10
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (7)..(7)
<223> OTHER INFORMATION: L at position 7 is (D)-Leucine.

<400> SEQUENCE: 10

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 11
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (8)..(8)
<223> OTHER INFORMATION: X at position 8 is (R)-Beta-2-Norleucine.

<400> SEQUENCE: 11

Ser Val Ser Glu Ile Gln Leu Xaa His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 12
<211> LENGTH: 34
```

```
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (8)..(8)
<223> OTHER INFORMATION: X at position 8 is (R*)-Beta-2-Norleucine.

<400> SEQUENCE: 12

Ser Val Ser Glu Ile Gln Leu Xaa His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 13
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (8)..(8)
<223> OTHER INFORMATION: X at position 8 is (S*)-Beta-2-Norleucine

<400> SEQUENCE: 13

Ser Val Ser Glu Ile Gln Leu Xaa His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 14
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (1)..(1)
<223> OTHER INFORMATION: S at position 1 is (R*) Beta-2 Serine.
<220> FEATURE:
<221> NAME/KEY: MOD_RES
<222> LOCATION: (7)..(7)
<223> OTHER INFORMATION: L at position 7 is (R*) Beta-2 Leucine.

<400> SEQUENCE: 14

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 15
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (1)..(1)
<223> OTHER INFORMATION: S at position 1 is (R*) Beta-2 Serine.
<220> FEATURE:
```

```
<221> NAME/KEY: MOD_RES
<222> LOCATION: (6)..(6)
<223> OTHER INFORMATION: Q at position 1 is (R*) Beta-2 Glutamine.

<400> SEQUENCE: 15

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 16
<211> LENGTH: 34
<212> TYPE: PRT
<213> ORGANISM: Homo sapiens

<400> SEQUENCE: 16

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 17
<211> LENGTH: 36
<212> TYPE: PRT
<213> ORGANISM: Artificial Sequence
<220> FEATURE:
<223> OTHER INFORMATION: Long-acting (LA)-PTH, a parathyroid hormone
      analog

<400> SEQUENCE: 17

Ala Val Ala Glu Ile Gln Leu Met His Gln Arg Ala Lys Trp Ile Gln
1               5                   10                  15

Asp Ala Arg Arg Arg Ala Phe Leu His Lys Leu Ile Ala Glu Ile His
            20                  25                  30

Thr Ala Glu Ile
        35

<210> SEQ ID NO 18
<211> LENGTH: 34
<212> TYPE: PRT
<213> ORGANISM: Artificial Sequence
<220> FEATURE:
<223> OTHER INFORMATION: Synthetic polypeptide BA058, also known as
      Abaloparatide, a parathyroid hormone-related protien analog drug
      used to treat osteoporosis.
<220> FEATURE:
<221> NAME/KEY: MOD_RES
<222> LOCATION: (29)..(29)
<223> OTHER INFORMATION: X at position 29 is selencysteine (i.e., "U").

<400> SEQUENCE: 18

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Xaa Lys Leu His
            20                  25                  30

Thr Ala

<210> SEQ ID NO 19
<211> LENGTH: 36
<212> TYPE: PRT
<213> ORGANISM: Homo sapiens
```

<400> SEQUENCE: 19

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile
        35

<210> SEQ ID NO 20
<211> LENGTH: 115
<212> TYPE: PRT
<213> ORGANISM: Artificial Sequence
<220> FEATURE:
<223> OTHER INFORMATION: Synthetic amino acid sequence.

<400> SEQUENCE: 20

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
            20                  25                  30

Val Ser Glu Ile Gln Leu Met His Asn Leu Gly Lys His Leu Asn Ser
        35                  40                  45

Met Glu Arg Val Glu Trp Leu Arg Lys Lys Leu Gln Asp Val His Asn
    50                  55                  60

Phe Val Ala Leu Gly Ala Pro Leu Ala Pro Arg Asp Ala Gly Ser Gln
65                  70                  75                  80

Arg Pro Arg Lys Lys Glu Asp Asn Val Leu Val Glu Ser His Glu Lys
                85                  90                  95

Ser Leu Gly Glu Ala Asp Lys Ala Asp Val Asn Val Leu Thr Lys Ala
            100                 105                 110

Lys Ser Gln
        115

<210> SEQ ID NO 21
<211> LENGTH: 84
<212> TYPE: PRT
<213> ORGANISM: Artificial Sequence
<220> FEATURE:
<223> OTHER INFORMATION: Synthetic amino acid sequence.

<400> SEQUENCE: 21

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 22
<211> LENGTH: 34
<212> TYPE: PRT
<213> ORGANISM: Artificial Sequence
<220> FEATURE:

```
<223> OTHER INFORMATION: Synthetic amino acid sequence.
<220> FEATURE:
<221> NAME/KEY: MOD_RES
<222> LOCATION: (1)..(1)
<223> OTHER INFORMATION: S at position 1 is (R*) Beta-2 Serine.

<400> SEQUENCE: 22

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 23
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (2)..(2)
<223> OTHER INFORMATION: V at position 2 is ( R*) Beta-2 Valine.

<400> SEQUENCE: 23

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 24
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (3)..(3)
<223> OTHER INFORMATION: S at position 2 is ( R*) Beta-2 Serine.

<400> SEQUENCE: 24

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 25
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (4)..(4)
<223> OTHER INFORMATION: E at position 4 is ( R*) Beta-2 Glutamic Acid.

<400> SEQUENCE: 25

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30
```

Asn Phe

<210> SEQ ID NO 26
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (5)..(5)
<223> OTHER INFORMATION: I at position 5 is ( R*) Beta-2 Isoleucine.

<400> SEQUENCE: 26

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 27
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (6)..(6)
<223> OTHER INFORMATION: Q at position 6 is ( R*) Beta-2 Glutamine.

<400> SEQUENCE: 27

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 28
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (7)..(7)
<223> OTHER INFORMATION: L at position 7 is ( R*) Beta-2 Leucine.

<400> SEQUENCE: 28

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 29
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (8)..(8)

<223> OTHER INFORMATION: X at position 8 is ( R*) Beta-2 Norleucine.

<400> SEQUENCE: 29

Ser Val Ser Glu Ile Gln Leu Xaa His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 30
<211> LENGTH: 34
<212> TYPE: PRT
<213> ORGANISM: Artificial Sequence
<220> FEATURE:
<223> OTHER INFORMATION: Synthetic polypeptide.
<220> FEATURE:
<221> NAME/KEY: MOD_RES
<222> LOCATION: (1)..(1)
<223> OTHER INFORMATION: S at position 1 is (S*) Beta-2 Serine.

<400> SEQUENCE: 30

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 31
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (2)..(2)
<223> OTHER INFORMATION: V at position 2 is (S*) Beta-2 Valine.

<400> SEQUENCE: 31

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 32
<211> LENGTH: 34
<212> TYPE: PRT
<213> ORGANISM: Artificial Sequence
<220> FEATURE:
<223> OTHER INFORMATION: Synthetic polypeptide.
<220> FEATURE:
<221> NAME/KEY: MOD_RES
<222> LOCATION: (3)..(3)
<223> OTHER INFORMATION: S at position 3 is (S*) Beta-2 Serine

<400> SEQUENCE: 32

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

```
<210> SEQ ID NO 33
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (4)..(4)
<223> OTHER INFORMATION: E at position 4 is (S*) Beta-2 Glutamic Acid.

<400> SEQUENCE: 33

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 34
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (5)..(5)
<223> OTHER INFORMATION: I at position 5 is (S*) Beta-2 Isoleucine.

<400> SEQUENCE: 34

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 35
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: 6MOD_RES
<222> LOCATION: (6)..(6)
<223> OTHER INFORMATION: Q at position 6 is (S*) Beta-2 Glutamine.

<400> SEQUENCE: 35

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 36
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (7)..(7)
<223> OTHER INFORMATION: L at position 7 is (S*) Beta-2 Leucine.

<400> SEQUENCE: 36
```

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 37
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (8)..(8)
<223> OTHER INFORMATION: X at position 1 is (S*) Beta-2 Norleucine.

<400> SEQUENCE: 37

Ser Val Ser Glu Ile Gln Leu Xaa His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 38
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (1)..(1)
<223> OTHER INFORMATION: S at position 1 is (S*) Beta-3 Serine.

<400> SEQUENCE: 38

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 39
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (2)..(2)
<223> OTHER INFORMATION: V at position 2 is (S*) Beta-3 Valine.

<400> SEQUENCE: 39

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 40
<211> LENGTH: 34
<212> TYPE: PRT
<213> ORGANISM: Artificial Sequence

```
<220> FEATURE:
<223> OTHER INFORMATION: Synthetic amino acid sequence.
<220> FEATURE:
<221> NAME/KEY: MOD_RES
<222> LOCATION: (3)..(3)
<223> OTHER INFORMATION: S at position 3 is (S*) Beta-3 Serine.

<400> SEQUENCE: 40

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 41
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (4)..(4)
<223> OTHER INFORMATION: E at position 4 is (S*) Beta-3 Glutamic Acid.

<400> SEQUENCE: 41

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 42
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (5)..(5)
<223> OTHER INFORMATION: I at position 5 is (S*) Beta-3 Isoleucine.

<400> SEQUENCE: 42

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 43
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (6)..(6)
<223> OTHER INFORMATION: Q at position 6 is (S*) Beta-3 Glutamine.

<400> SEQUENCE: 43

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
```

```
<210> SEQ ID NO 44
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (7)..(7)
<223> OTHER INFORMATION: L at position 7 is (S*) Beta-3 Leucine.

<400> SEQUENCE: 44

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 45
<211> LENGTH: 34
<212> TYPE: PRT
<213> ORGANISM: Artificial Sequence
<220> FEATURE:
<223> OTHER INFORMATION: Synthetic amino acid sequence.
<220> FEATURE:
<221> NAME/KEY: MOD_RES
<222> LOCATION: (8)..(8)
<223> OTHER INFORMATION: M at position 8 is (S*) Beta-3 Methionine.

<400> SEQUENCE: 45

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe
```

ANALOGUES OF PARATHYROID HORMONE (1-34) THAT FUNCTION AS AGONISTS OF THE PARATHYROID HORMONE RECEPTOR-1 AND DISPLAY MODIFIED ACTIVITY PROFILES

CROSS-REFERENCE TO RELATED APPLICATIONS

This is a continuation of application Ser. No. 16/109,114, filed Aug. 22, 2018 (now abandoned), which is a continuation-in-part of application Ser. No. 14/312,012, filed Jun. 23, 2014 (now U.S. Pat. No. 10,501,518, issued Dec. 10, 2019), which claims priority to provisional application Ser. No. 61/940,124, filed Feb. 14, 2014, and to provisional application Ser. No. 61/838,307, filed Jun. 23, 2013, all which are incorporated herein by reference, and also claims priority to provisional application Ser. No. 62/548,442, filed Aug. 22, 2017, which is incorporated herein by reference.

FEDERAL FUNDING STATEMENT

This invention was made with government support under DK011794 and GM056414 awarded by the National Institutes of Health. The Government has certain rights in the invention.

BACKGROUND

Proper function of individual cells and entire organisms depends upon information transfer from the extracellular environment to the cytoplasm. Most signals must be transduced via proteins that span cellular membranes. Many receptor proteins do not act as simple, binary "toggle switches," with only signaling-active and signaling-inactive states. Rather, they behave in vivo as nuanced interpreters of molecular information. This behavior enables the transmission of diverse messages based on variations in agonist structure. "Biased agonism" is one widely-studied manifestation of this complexity that has been documented for multiple G protein-coupled receptors (GPCRs).[1,2] Signal transduction via these GPCRs involves multiple intracellular partners, only some of which are G proteins. A natural agonist activates these alternative signaling pathways in a given proportion, for a given cell type and environment. Other agonists are designated as biased relative to this benchmark if they lead to a different balance of signal intensities among the available pathways.[3] These differences in signal transduction pattern can arise from subtle agonist-dependent variations in receptor conformation.[4]

The biased agonism paradigm is not the only mechanism by which diversity in GPCR signaling can arise from variations in agonist-bound receptor conformation. The parathyroid hormone receptor-1 (PTHR-1), for example, has two distinct functional states. These are depicted schematically in FIG. 1. The RG functional state, shown to the right in FIG. 1, forms when the intracellular portion contacts a given G protein (designated $G\alpha_{ND}$ in FIG. 1). In contrast, the $R^0$ functional state, shown to the left in FIG. 1, forms independent of G protein association.[5,6] An agonist's affinity for the RG state is predicted to correlate with PTHR-1 activation potency, while an agonist's $R^0$ affinity correlates with the duration of some in vivo responses.[7,8] Natural agonists for PTHR-1 include parathyroid hormone (PTH) and parathyroid hormone-related protein (PTHrP), which display similar affinity for the RG state but differ in their affinity for the $R^0$ state.[7] This behavior cannot be described as biased agonism because PTH and PTHrP seem to activate the same intracellular signaling mechanisms,[9] but there is a clear mechanistic parallel to the bias paradigm in that agonists with different receptor-state selectivities cause different biological effects.[7,8,10]

The signaling duration of PTHR1 is highly ligand dependent. The transient PTHR1 activation by PTHrP is primarily confined to cell membrane, which follows the classic GPCR signaling model. On the other hand, PTHR1 activation by PTH is more prolonged. As noted above, such a distinction of signaling mode was initially explained by a "conformational selectivity" model, which involves two conformational states, G protein-dependent (RG) versus G protein-independent (R0). It is proposed that ligands with higher R0 binding affinity have longer receptor residence time and thereby produce more sustained signaling response via more cycles of R0-to-RG isomerization. In parallel, the functional diversity of β-arrestin ("βarr") in GPCR signaling has received increasing investigation in recent years. Different from its classic role as signaling desensitizer, βarr was also found to act as the scaffold protein to assemble the signaling complex. In the context of PTHR1 signaling, it was discovered that sustained cAMP activation can originate from the endosome after internalization of the ligand/GPCR/βarr ternary complex. In such a signaling mode, βarr plays a key role causing receptor internalization and assembling the downstream signaling cascade. PTHR1 agonists with high R0-binding affinity, such as PTH and LA-PTH, appear to favor the formation of the ternary complex.

Receptor state-selective agonists are highly prized because these molecules can serve as powerful tools for elucidating signal-transduction mechanisms, and they may give rise to therapeutic agents with minimal deleterious side effects.[12] At present, there is no way to design such agonists via rational methods.

In terms of mammalian disease states, including humans, the umbrella term hypoparathyroidism is used to designate any decreased function of the parathyroid glands with concomitant underproduction of PTH. This then leads to low levels of calcium in the blood. The main symptoms of hypoparathyroidism are the result of the low blood calcium level, which interferes with normal muscle contraction and nerve conduction. As a result, people with hypoparathyroidism experience a number of unsettling symptoms, including paresthesia (an unpleasant tingling sensation around the mouth and in the hands and feet), muscle cramps, and tetany (severe spasms that affect the hands and feet). Many subjects suffering from hypoparathyroidism also report somewhat vague but pervasive symptoms such as fatigue, headaches, bone pain and insomnia. Chronic hypoparathyroidism is conventionally treated with vitamin D analogs and calcium supplementation. However, such treatments are contra-indicated in many patients due to potential renal damage. The N-terminal fragment of parathyroid hormone, PTH (1-34), has full biological activity. Teriparatide (marketed in the U.S. by Eli Lilly & Co. under the trademark "Forted") is a recombinant form of PTH approved for use in the treatment of osteoporosis.

SUMMARY OF THE INVENTION

G protein-coupled receptors (GPCRs), the targets of many current therapeutic agents, can adopt multiple activated states, and there is increasing interest in synthetic molecules that display altered receptor-state selectivity patterns relative to natural agonists. Disclosed herein are backbone-modified analogs of a well-known peptide agonist, PTH(1-34). The PTH (1-34) analogues described herein are biased toward Gs activation/cAMP production relative to β arrestin recruitment. The analogs were generated via systematic replacement of selected α-amino acid residues with either β-amino acid residues or with unnatural D-stereoisomer α-amino acid residues. Two distinct states of PTHR-1 with high agonist affinity are known, and this system was used to assess the impact of backbone modification on binding preferences for the alternative receptor conformations. The results show that biased agonism can be achieved via this strategy. The resulting variations in agonist properties can give rise to distinct behaviors in vivo.

Thus, disclosed herein is a method to make unnatural PTHR-1 peptide agonists which exhibit biased agonism activity. The method comprises determining or acquiring the α-amino acid sequence of a first PTHR-1 peptide agonist that comprises α-amino acid residues, and then fabricating an analog of the first PTHR-1 peptide agonist in which at least one natural L-stereoisomer α-amino acid residue in position 6, 7, or 8 from the N-terminus of the PTHR-1 is replaced with a β-amino acid residue or an unnatural D-stereoisomer α-amino acid residue. The natural α-amino acid residue may optionally be replaced with a β-amino acid or a D-α-amino acid residue having the same side-chain as the natural α-amino acid residue it replaces. Alternatively, at least one of the natural α-amino acid residues may optionally be replaced with a cyclically constrained β-amino acid residue. The same substitutions may also be made at positions 1 and 2.

Also disclosed herein are the resulting unnatural, isolated peptide analogs. Thus, disclosed herein are unnatural, isolated peptide analogs comprising PTH, a parathyroid hormone receptor (PTHR-1, PTHR-2) agonist- or antagonist- or inverse agonist effective fragment of PTH, a parathyroid hormone related protein (PTHrP), a PTHR-1 or PTHR-2 agonist-, antagonist-, or inverse agonist-effective fragment of PTHrP, M-PTH, a PTHR-1 or PTHR-2 agonist-, antagonist-, or inverse agonist-effective fragment of M-PTH, abaloparatide (BA058), or a PTHR-1 or PTHR-2 agonist-, antagonist-, or inverse agonist-effective fragment of BA058, in which at least one natural L-stereoisomer α-amino acid residue in position 6, 7, or 8 from the N-terminus of the protein or fragment thereof is replaced with a β-amino acid residue or an unnatural D-stereoisomer α-amino acid residue. As in the first embodiment, the same substitutions may also be made at positions 1 and 2.

Salts of the foregoing peptide analogs are also within the scope of this disclosure.

In another version, the PTH analogs comprise thirty four (34) N-terminal residues of a mammalian parathyroid hormone, PTH(1-34), in which at least one natural L-stereoisomer α-amino acid residue in position 7 or 8 from the N-terminus of the PTH(1-34) is replaced with a β-amino acid residue or an unnatural D-stereoisomer α-amino acid residue.

Specific PTH analogs disclosed herein include:

```
                                         (SEQ. ID. NO: 1)
Ligand 1:  SVSEIQLMHNLGKHLNSMERVEWLRKKLQDVHNF (SEQ. ID. NO: 2)
Ligand 2:  SVSEIQLMHNLGKHLNSMERVEWLRKKLQDVHNF (SEQ. ID. NO: 3)
Ligand 3:  SVSEIQLMHNLGKHLNSMERVEWLRKKLQDVHNF (SEQ. ID. NO: 4)
Ligand 4:  SVSEIQLMHNLGKHLNSMERVEWLRKKLQDVHNF
```

```
                                         (SEQ. ID. NO: 5)
Ligand 5:  SVSEIQLMHNLGKHLNSMERVEWLRKKLQDVHNF (SEQ. ID. NO: 6)
Ligand 6:  SVSEIQLMHNLGKHLNSMERVEWLRKKLQDVHNF (SEQ. ID. NO: 7)
Ligand 7:  SVSEIQLMHNLGKHLNSMERVEWLRKKLQDVHNF (SEQ. ID. NO: 8)
Ligand 8:  SVSEIQLMHNLGKHLNSMERVEWLRKKLQDVHNF (SEQ. ID. NO: 9)
Ligand 9:  SVSEIQLMHNLGKHLNSMERVEWLRKKLQDVHNF (SEQ. ID. NO: 10)
Ligand 10: SVSEIQLMHNLGKHLNSMERVEWLRKKLQDVHNF (SEQ. ID. NO: 11)
Ligand 11: SVSEIQL"LHNLGKHLNSMERVEWLRKKLQDVHNF (SEQ. ID. NO: 12)
Ligand 12: SVSEIQL'LHNLGKHLNSMERVEWLRKKLQDVHNF (SEQ. ID. NO: 13)
Ligand 13: SVSEIQL'LHNLGKHLNSMERVEWLRKKLQDVHNF (SEQ. ID. NO: 14)
Ligand 14: SVSEIQLMHNLGKHLNSMERVEWLRKKLQDVHNF (SEQ. ID. NO: 15)
Ligand 15: SVSEIQLMHNLGKHLNSMERVEWLRKKLQDVHNF (SEQ. ID. NO: 16)
PTH (1-34) SVSEIQLMHNLGKHLNSMERVEWLRKKLQDVHNF
bold = (R*) β² amino acid residue
bold, underline = (S*) β² amino acid residue
bold, double-underline = (S*) β³ amino acid residue
bold, italics = (D)- α-amino acid residue
nL = (R) - β²-Nle
```

The PTH analogs disclosed herein may be biased agonists of parathyroid hormone receptor-1.

Also disclosed herein are pharmaceutical compositions for treating hypoparathyroidism. The composition comprises a parathyroid hormone receptor agonist-effective amount of a compound or salt thereof as disclosed herein in combination with a pharmaceutically suitable carrier. Also disclosed herein is a method of treating hypoparathyroidism in a mammalian subject, including a human subject. The method comprising administering to the subject a parathyroid hormone receptor agonist-effective amount of a pharmaceutical composition as described herein.

BRIEF DESCRIPTION OF THE DRAWINGS

FIG. 4 discloses the sequences of exemplary ligands disclosed and claimed herein and their respective activities to induce cAMP activity.

DETAILED DESCRIPTION

Abbreviations and Definitions

Figure 1:
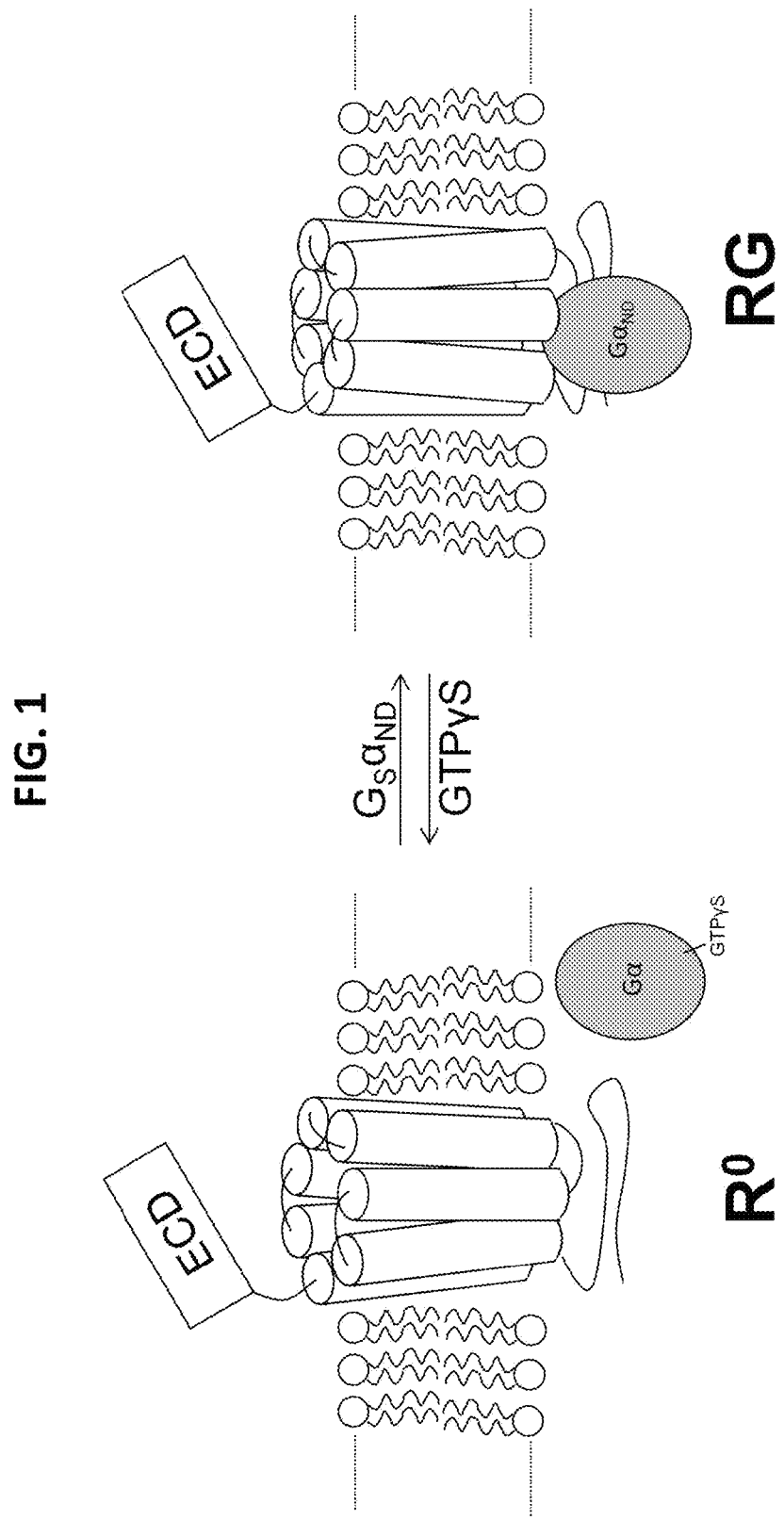
FIG. 1 is a schematic diagram of the G-protein uncoupled (R⁰) and coupled (RG) conformational states of PTHR-1. "ECD" is extracellular domain.

Agonist, Antagonist, Inverse Agonist: An inverse agonist is an agent that binds to the same receptor as an agonist but induces a pharmacological response opposite to that agonist. A prerequisite for an inverse agonist response is that the receptor must have a constitutive level of activity in the absence of any ligand. An agonist increases the activity of a receptor above its basal level, whereas an inverse agonist decreases the activity below the basal level. An antagonist binds to the receptor and blocks the activity of both agonists and inverse agonists.

"Cyclically constrained" when referring to a β-amino acid or β-amino acid residue means a β-amino acid or β-amino acid residue in which the α-position and β-position carbon atoms in the backbone of the β-amino acid are incorporated into a substituted or unsubstituted $C_4$ to $C_{10}$ cycloalkyl, cycloalkenyl, or heterocycle moiety, wherein heterocycle moieties may have 1, 2, or 3 heteroatoms selected from the group consisting of N, S, and O. Generally preferred cyclically constrained β-amino acids have the α-position and β-position carbon atoms in the backbone incorporated into a substituted or unsubstituted $C_5$ to $C_8$ cycloalkyl, cycloalkenyl, or heterocycle moiety having one or more N, S, or O atoms as the heteroatom. Within any given PTH analog, the cyclically constrained β-amino acid residues may be the same or different.

DIEA=N,N-diisopropylethylamine.
DMF=dimethylformamide.
GPCR=G protein-coupled receptor.
HBTU=2-(1H-benzotriazole-1-yl)-1,1,3,3-tetramethyluronium hexafluorophosphate.
HOBt=N-hydroxybenzotriazole.
MALDI-TOF-MS=matrix-assisted laser desorption/ionization time-of-flight mass spectrometry.

PTH=mammalian parathyroid hormone (including human PTH), its proprotein, its preproprotein, and any PTHR-1 agonist-effective fragment thereof. In humans, the corresponding PTH gene encodes and expresses a preproprotein comprising the amino acid sequence:

(SEQ. ID. NO: 20)
MIPAKDMAKVMIVMLAICFLTKSDGKSVKKRSVSEIQLMHNLGKHLNSME

RVEWLRKKLQDVHNFVALGAPLAPRDAGSQRPRKKEDNVLVESHEKSLGE

ADKADVNVLTKAKSQ.

After post-translational processing, human PTH comprises the amino acid sequence (SEQ. ID. NO: 21)
SVSEIQLMHNLGKHLNSMERVEWLRKKLQDVHNFVALGAPLAPRDAGSQR

PRKKEDNVLVESHEKSLGEADKADVNVLTKAKSQ.

See U.S. National Center for Biotechnology Information (NCBI) reference sequence NP_000306.

PTHR-1=parathyroid hormone receptor 1. hPTHR-1 designates the human version of the receptor; rPTHR-1 designates the rat version of the receptor. The prefix or suffix WT in combination with either designates "wild-type."

PTHrP=parathyroid hormone-related protein (SEQ. ID. NO: 19)

TFA=trifluoroacetic acid.
TBS=tris-buffered saline (i.e., tris(hydroxymethyl)aminomethane).
WT=wild-type.

Amino acid residues in the analogues disclosed herein that also appear in the corresponding natural protein/polypeptide are present in their L configuration. Unnatural α-amino acid substitutions are present in their D configuration. The terms "peptide" and "polypeptide" are used synonymously and refer to a polymer of amino acids which are linked via amide linkages. β-amino acid residues may be linear, unsubstituted, or substituted at the α- or β-position carbon atoms of the backbone (i.e., at the $β^2$ or $β^3$ carbon atoms) or may be conformationally constrained by a cyclic group encompassing the α and β backbone carbon atoms of the inserted β-amino acid residue. While not required, it is preferred that the β-amino acid residues are corresponding $β^3$ versions of the α-amino acid residues they replace. That is, the side-chain on the β-position carbon (the $β^3$ carbon) in the β-amino acid residue is the same as the side-chain on the α-amino acid residue it replaces and the α-position carbon (the $β^2$ carbon) in the β-amino acid residue is unsubstituted.

"Pharmaceutically suitable salts" means salts formed with acids or bases the addition of which does not have undesirable effects when administered to mammals, including humans. Preferred are the salts with acids or bases listed in the U.S. Pharmacopoeia (or any other generally recognized pharmacopoeia) for use in humans. A host of pharmaceutically-suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures. Pharmaceutically-suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene bis b hydroxynaphthoates, gentisates, isethionates, di p toluoyltartrates, methane sulphonates, ethanesulphonates, benzenesulphonates, p toluenesulphonates, cyclohexylsulphamates, quinates, and the like. Base addition salts include those derived from alkali or alkaline earth metal bases or conventional organic bases, such as triethylamine, pyridine, piperidine, morpholine, N methylmorpholine, and the like. Other suitable salts are found in, for example, Handbook of Pharmaceutical Salts, P. H. Stahl and C. G. Wermuch, Eds., © 2011, Wiley-VCH (Zurich, Switzerland) ISBN: 978-3906390512, which is incorporated herein by reference.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods, compounds and compositions of the present invention can comprise, consist of, or consist essentially of the essential elements and limitations of the method described herein, as well as any additional or optional ingredients, components, or limitations described herein or otherwise useful in synthetic organic chemistry, pharmacy, pharmacology, and the like.

Overview:

Alternative activated conformations of a receptor protein are likely to differ from one another in subtle ways.[4] Thus, making subtle modifications to a natural agonist could be fruitful for making compounds with diverse selectivities among functional receptor states. In the present invention, an unconventional strategy was used in which the backbone of a natural PTHR-1 agonist was altered, rather than the side-chain complement. The results show that backbone-modification can rapidly identify potent agonists with divergent receptor state selectivity patterns relative to a prototype peptide.

More specifically, the initial studies that yielded the compounds disclosed and claimed herein were conducted to determine whether there is a correlation between βarr recruitment and receptor residence time of a PTHR1 agonist. The initial studies were thus conducted in two steps. First, the functional selectivity (Gs activation as indicated by cAMP production vs. βarr recruitment) of several PTHR1 agonists that display substantial differences in signaling duration were evaluated. Second, novel PTHR1 agonists were designed that have high functional selectivity and evaluated the signaling duration of these biased agonists.

Design of PTH(1-34) Analogs:

PTH is an 84-residue protein that controls key physiological processes, including the maintenance of extracellular levels of calcium and phosphate.[9] The N-terminal fragment PTH(1-34) matches full-length PTH in potency and efficacy at PTHR-1 and is the active ingredient in the osteoporosis drug teriparatide.[11] A crystal structure of the human PTHR-1 extracellular domain (ECD) bound to PTH(15-34) reveals that this segment forms an α-helix upon association with the receptor.[12] The bioactive conformation of the N-terminal portion of PTH is unknown. PTH(1-34) analogs containing unnatural residue substitutions in the N-terminal region were fabricated and their in vitro and in vivo activity as PTHR-1 agonists explored. Exemplary α/β-peptide analogs according to the present invention (working examples) are shown in FIG. 4. Native α residues in the wild-type PTH were replaced with $β^3$ homologs. Thus, in the exemplary compounds the natural side chain sequence was maintained in the resulting α/β-peptides, but the backbone contained additional $CH_2$ units.

Receptor Binding and Activation:

Well-established radio-ligand-displacement assays[5-7] were used to determine whether the α→β and L→D α replacements lead to variations in affinities for the $R^0$ or RG state of hPTHR-1 relative to the prototype α-peptide PTH (1-34)[14,15] Agonist activity was determined by monitoring cAMP production in HEK293 cells that stably express PTHR-1 and the GloSensor-brand cAMP reporter and PTHR-1.[16]

The results of the binding and activity assays support the hypothesis that subtle modification of a prototype α-peptide via α→β and/or L→D α replacements enables the discovery of agonists with variations in receptor-state affinity profile relative to the α-peptide itself.

Figure 2:
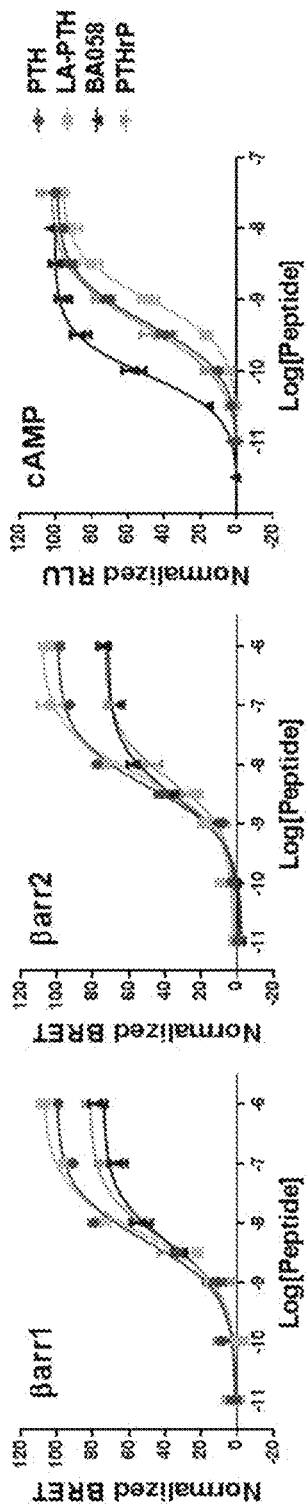
FIG. 2 depicts graphs and a corresponding table reporting the EC50 and Emax of PTHR1 agonists PTH, LA-PTH, BA058 and PTHrP for cAMP signaling and β-arrestin (βarr) recruitment.
Figure 3:
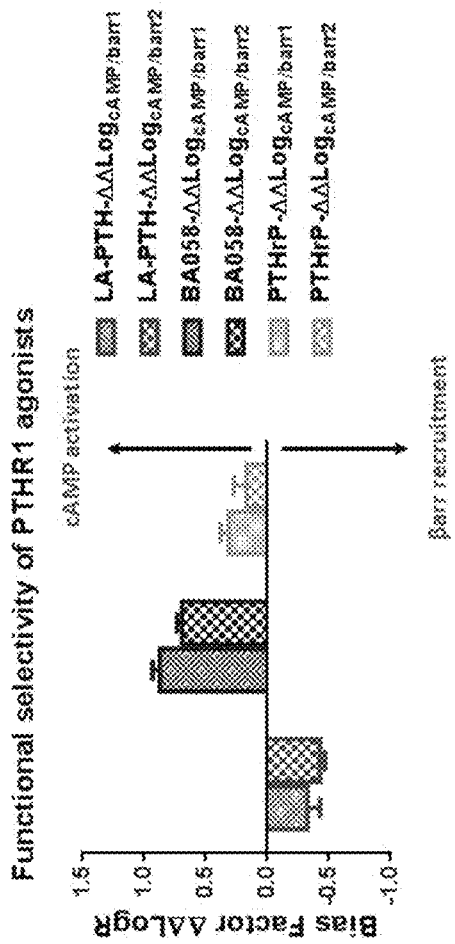
FIG. 3 is a histogram and corresponding table reporting the functional selectivity of various PTHR1 agonists that display distinctly different signaling durations.

Functional Selectivity of Reported R0- and RG-Selective PTHR1 Agonists:

Relative to PTH (1-34) (SEQ. ID. NO: 16), BA058 (also known as abaloparatide; SEQ. ID. NO: 18; see FIG. 2) and PTHrP (1-36) (SEQ. ID. NO: 19; see FIG. 2) display low and moderate R0 affinity respectively, and these agonists induce signaling bias toward Gs/cAMP activation relative to PTH (1-34). The functional selectivity of BA058 is more significant than that of PTHrP. In contrast, LA-PTH (SEQ. ID. NO: 17; see FIG. 2), which has high R0 affinity and induces prolonged endosomal signaling, appears to be slightly biased toward βarr recruitment. LA-PTH is a long-acting PTH analog. See, for example, Shimuzu et al. (2016) "Pharmacodynamic Actions of a Long-Acting PTH Analog (LA-PTH) in Thyroparathyroidectomized (TPTX) Rats and Normal Monkeys," *J Bone Miner Res.* 31(7):1405-12. All four ligands show similar potency (EC50) in terms of βarr recruitment, but PTHrP and BA058 display a lower efficacy βarr recruitment maximum than do PTH and LA-PTH. See FIGS. 2 and 3. The top panel of FIG. 2 provides the amino acid sequences for PTH(1-34), LA-PTH, BA058, and PTHrP. The middle panels in FIG. 2 are graphs depicting, from left-to-right: βarr1 and βarr2 recruitment, presented as normalized BRET signals (bioluminescence resonance energy transfer) as a function of the log of the peptide concentration, and cAmp activation presented as normalized RLU signals (relative light units) as a function of the log of the peptide concentration. Red=PTH. Orange=LA=LA–PTH. Blue=BA058. Green=PTHrP. (BRET assays are well known and suitable kits are available commercially. See, for example, Promega's "NanoBRET" kits, catalogs nos. N1821 and N1811; Promega Corporation, Fitchburg, Wis.). The table at the bottom of FIG. 2 presents the pEC50 and Emax values for the Purl and βarr2 recruitment and cAMP activation. FIG. 3 presents the data for the bias of the activity—either toward βarr recruitment or cAMP activation. As seen in the histogram in FIG. 3, the activity of LA-PTH is biased toward βarr1 and βarr2 recruitment relative to cAMP activation. In contrast, BA058 and PTHrP are both biased toward cAMP activation relative to both βarr1 and βarr2 recruitment. The table in FIG. 3 presents the bias factors for LA-PTH, BA058, and PTHrP.

Discovery of Highly G-Protein-Biased Signaling ("Gs") PTHR1 Agonists with Good Potency Via N-Terminal Modification of PTH:

In this work, it was found that several positions of N-terminal PTH can tolerate $\beta^2$ and/or $\beta^3$ amino acid substitutions. New PTHR1 agonists having high functional selectivity and good ligand potency were fabricated as a result. See FIG. 4. The chart on the left of FIG. 4 lists N-terminal amino acid positions on the Y-axis, and then indicates on the X-axis what types of amino acid substitutions at that amino acid position are tolerated with respect to the ability of the resulting peptide to activate cAMP production. The substitutions explores were $\alpha \rightarrow (R^*)-\beta^2$, $\alpha \rightarrow (S^*)\beta^2$, $\alpha \rightarrow (S^*)-\beta^3$, (L)-$\alpha \rightarrow$(D)-$\alpha$ Other N-terminal sites were also evaluated, but β substitutions at these sites generally led to a drop in potency and efficacy reduction for cAMP production and β arrestin recruitment.

Among Ligands 1-7 (SEQ. ID. NOS: 1-7, respectively), only Ligand 6, resulting from the incorporation of $(S^*)-\beta^2$Ile at the $5^{th}$ position of PTH, induces appreciable functional selectivity toward Gs/cAMP; Ligands 1-5 and 7 do not show significant signaling bias relative to PTH (1-34) (SEQ. ID. NO: 14). See Table 1.

TABLE 1

Bias Factors of Ligands 1-7

| | $\Delta\Delta LogR_{cAMP/\beta arr1}$ | $\Delta\Delta LogR_{cAMP/\beta arr2}$ |
|---|---|---|
| Ligand 1 | 0.02 ± 0.06 | 0.12 ± 0.10 |
| Ligand 2 | 0.01 ± 0.17 | 0.14 ± 0.07 |
| Ligand 3 | 0.15 ± 0.13 | 0.33 ± 0.08 |
| Ligand 4 | 0.24 ± 0.16 | 0.16 ± 0.16 |
| Ligand 5 | 0.11 ± 0.08 | 0.14 ± 0.09 |
| Ligand 6 | 0.63 ± 0.10 | 0.73 ± 0.11 |
| Ligand 7 | 0.29 ± 0.13 | 0.41 ± 0.06 |

Figure 5:
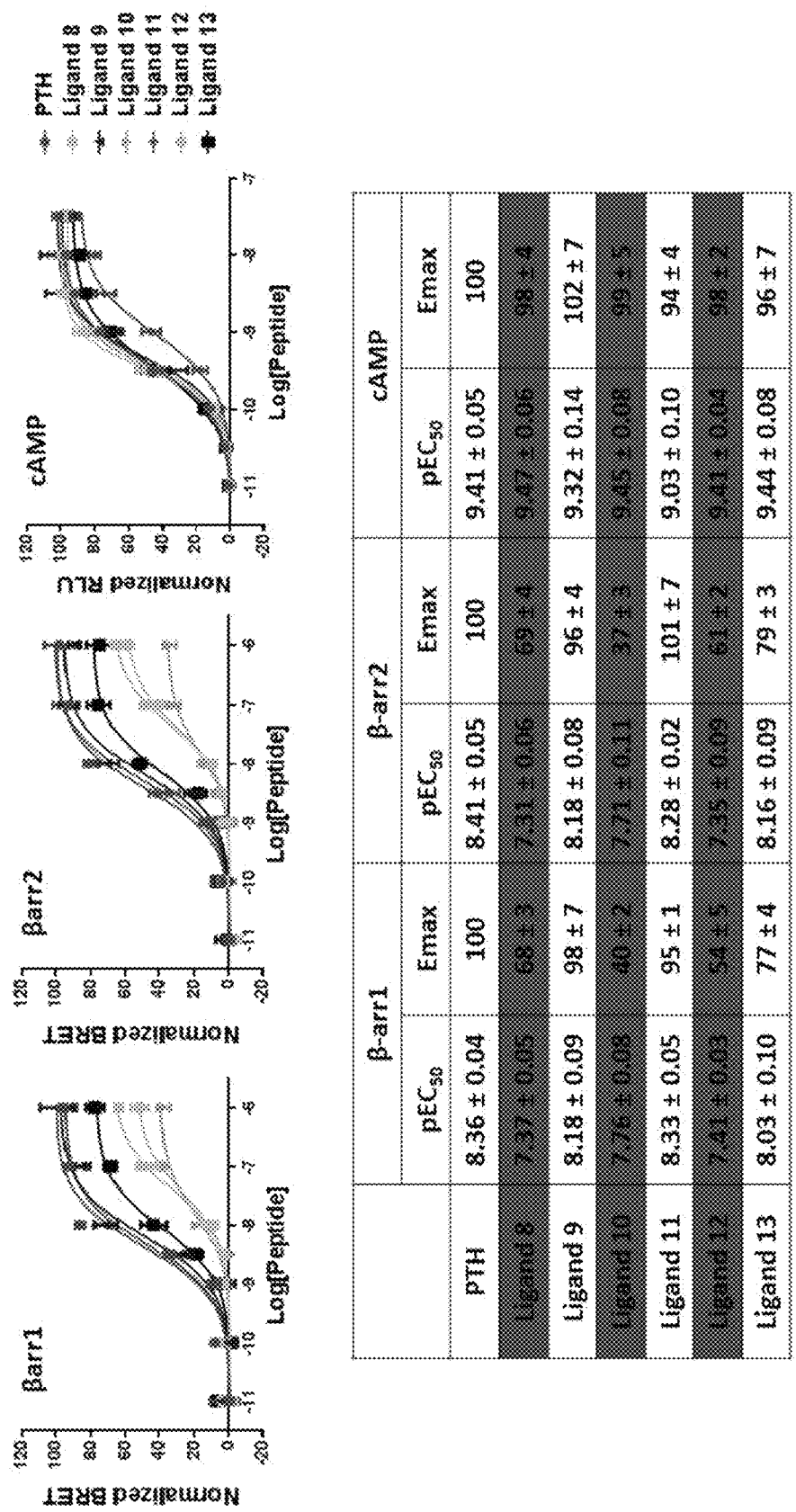
FIG. 5 depicts graphs and a corresponding table reporting the EC50 and Emax of PTHR1 agonists Ligands 8-13 (SEQ. ID. NOS: 8-13) for cAMP signaling and β-arrestin (βarr) recruitment.

In contrast, the $7^{th}$ and $8^{th}$ positions from the N-terminus of PTH(1-34) (explored in Ligands 8-13; SEQ. ID. NOS: 8-13, respectively) are sensitive spots for high functional selectivity. See FIG. 5. Incorporating $(R^*)-\beta^2$Leu/(D)-Leu at the $7^{th}$ position or $(R^*)-\beta^2$Nle at the $8^{th}$ position leads to high Gs-biased agonism. In contrast, $(S^*)-\beta^2$Leu at the $7^{th}$ position or $(S^*)-\beta^2$Nle/(L)-Nle at $8^{th}$ position does not induce significant signaling bias. (D)-Nle is poorly tolerated at the $8^{th}$ position for both cAMP signaling and βarr recruitment. The top panels in FIG. 5 are graphs depicting, from left-to-right: βarr1 and βarr2 recruitment, presented as normalized BRET signals as a function of the log of the peptide concentration, and cAmp activation presented as normalized RLU signals as a function of the log of the peptide concentration. Red circles=PTH(1-34). Yellow squares=Ligand 8. Blue upward triangles=Ligand 9. Green downward triangles=Ligand 10. Purple diamonds=Ligand 11. Green circles=Ligand 12. Black squares=Ligand 13. The table at the bottom of FIG. 5 presents the pEC50 and Emax values for the βarr1 and βarr2 recruitment and cAMP activation.

Figure 6:
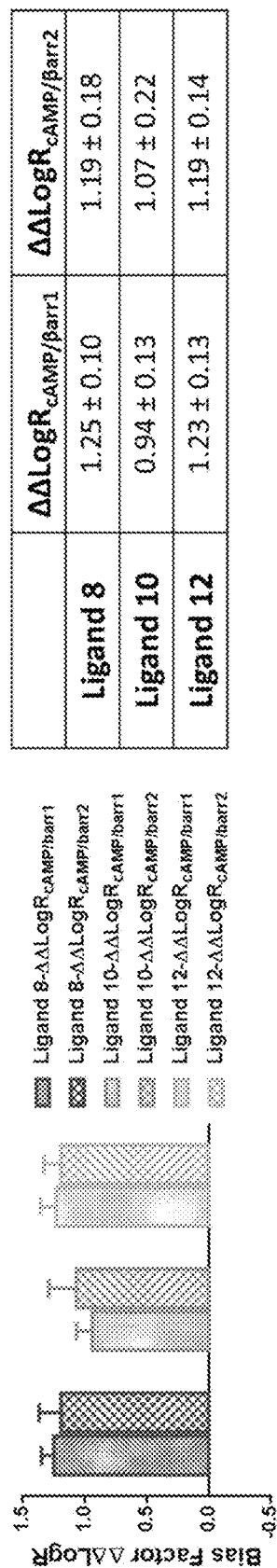
FIG. 6 is a histogram and corresponding table showing the bias factors of Ligands 8, 10, and 12 (SEQ. ID. NOS: 8, 10, and 12).

As seen in the histogram in FIG. 6, the signaling activities of Ligands 8, 10, and 12 are all strongly biased toward cAMP activation relative to both βarr1 and βarr2 recruitment. The table in FIG. 6 presents the bias factors for Ligands 8, 10, and 12.

Washout Assay of Gs-Biased PTHR1 Agonists:

Additional cell-based assays were pursued to elucidate the variation among in vivo responses observed for Ligands 8, 10, and 12, as contrasted to PTH(1-34). These "washout assays"[7,8,21] assess the ability of the peptides to form stable ligand-receptor complexes capable of stimulating prolonged cAMP responses. The ability of a peptide to elicit prolonged cAMP responses via PTHR-1 following washout typically correlates with the affinity of that peptide for the $R^0$ state.[7,8,21]

Figure 7:
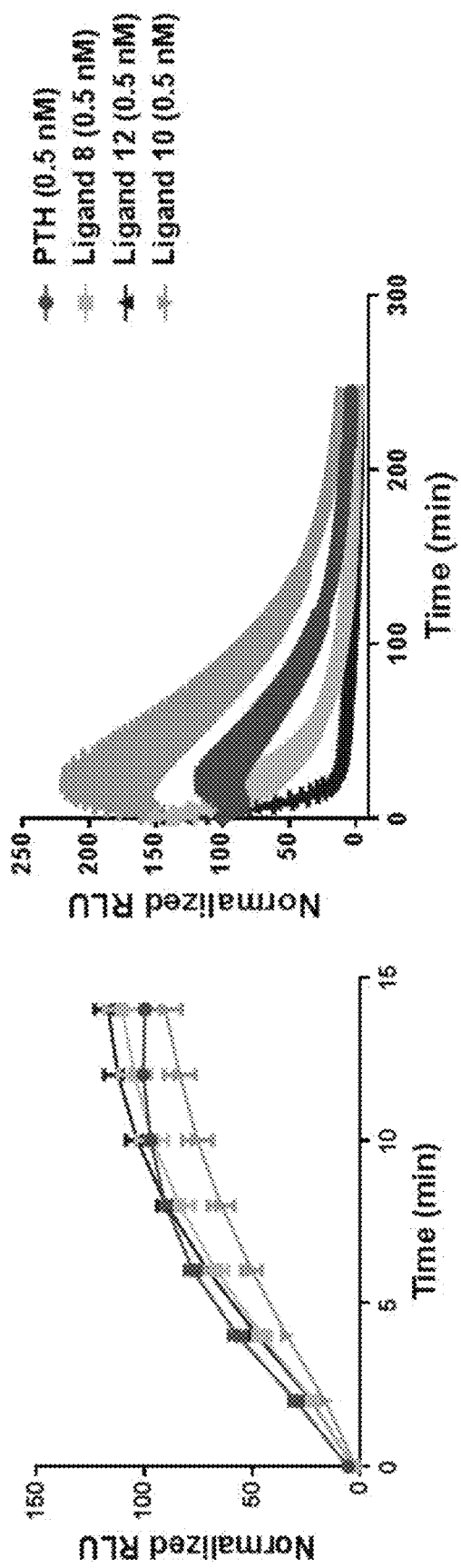
FIG. 7 depicts two graphs reporting the results of washout assays on Ligands 8, 10, and 12 (SEQ. ID. NOS: 8, 10, and 12).

The three highly Gs-biased PTHR1 agonists, Ligands 8, 10, and 12, were tested in the washout assay. See FIG. 7. Interestingly, they displayed very different signaling durations. Both 8 and 12 induced more transient signaling than PTH (1-34) (FIG. 7, left-hand panel), while the signaling duration of 10 was more prolonged than that of PTH (1-34) (FIG. 7, right-hand panel). These results suggest that the signaling duration of a PTHR1 agonist cannot be predicted from its functional selectivity.

Figure 8:
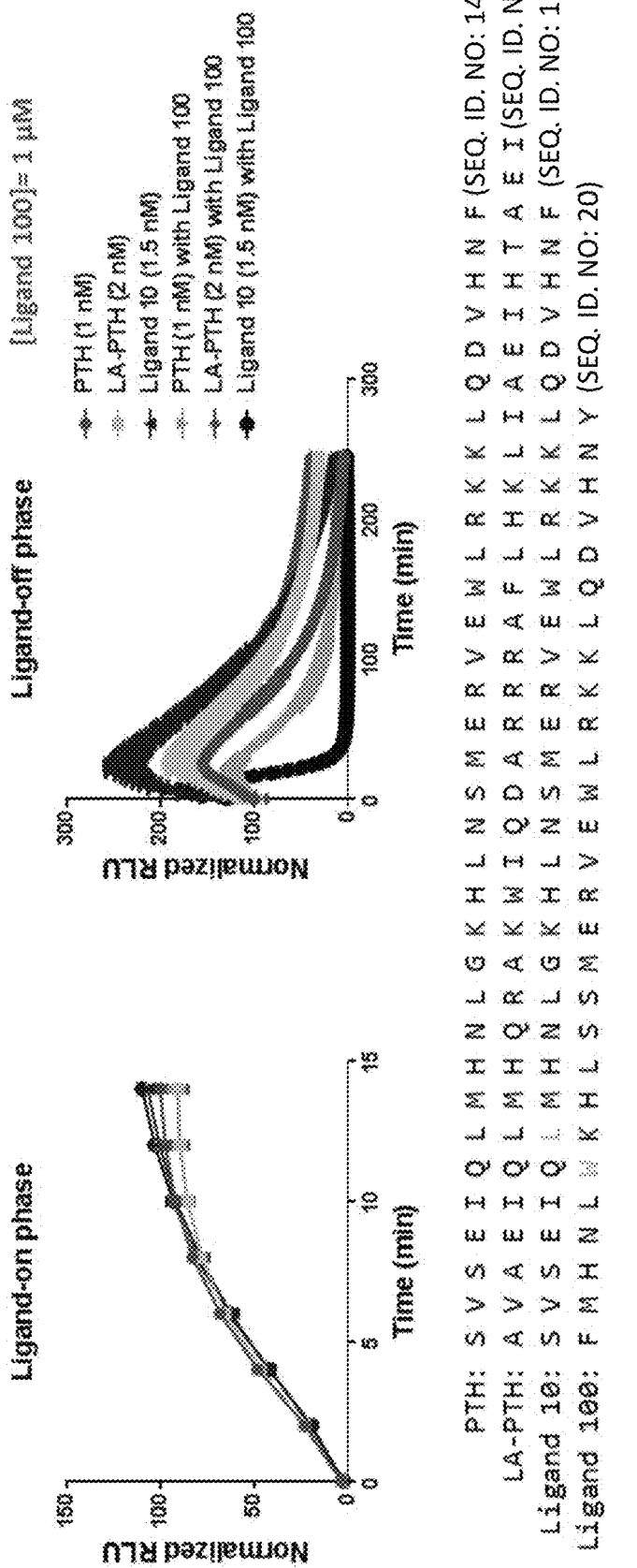
FIG. 8 depicts a matched pair of graphs ("Ligand-on phase" vs. "Ligand-off phase") reporting the effect of competitive antagonism on ligand signaling duration.

Utility of Highly Gs-Biased PTHR1 Agonists:

Gs-biased agonists of PTHR1 that cause transient receptor activation, like Ligands 8 and 12, useful for treating osteoporosis. Additionally, Gs-biased agonists that induce prolonged signaling duration, like Ligand 10, are useful for treating hypoparathyroidism. Without being limited to any underlying mechanism or biologicaly phenomenon, the sustained cAMP activation from a highly Gs-biased agonist, such as Ligand 10, could result from receptors that remain at the cell surface. This is because the relatively poor βarr recruitment ability of such a ligand should inhibit receptor internalization. (In contrast, sustained cAMP production induced by PTH (1-34) or LA-PTH involves internalized receptors). To test this hypothesis, a modified washout assay was designed in which the signaling durations of several PTHR1 agonists were compared in the presence of and in the absence of a non-internalized competitive antagonist, (D)-Trp$^{12}$, Tyr$^{34}$-bpTH (7-34). The results of this washout assay are shown in FIG. 8. In the experiment, the antagonist ligand was introduced to the cells in the "ligand-off" phase. Compared to LA-PTH and PTH, Ligand 10 displayed a very striking change of signaling duration upon the introduction of the competitive antagonist. This strongly indicates that this biased agonist mainly stays at the cell surface and is highly defective in inducing PTHR1 internalization.

Previous research shows that LA-PTH has a very short lifetime in the bloodstream despite its prolonged signaling effect; this behavior has been explained by proposing that LA-PTH is very effective in inducing internalization of the receptor-agonist complex and this internalization removes LA-PTH from the bloodstream. If this hypothesis is correct, then it is possible that a highly Gs-biased agonist would have a long lifetime in the bloodstream, relative to LA-PTH, which might lead to an improvement in therapeutic effect for hypoparathyroidism.

Figure 9:
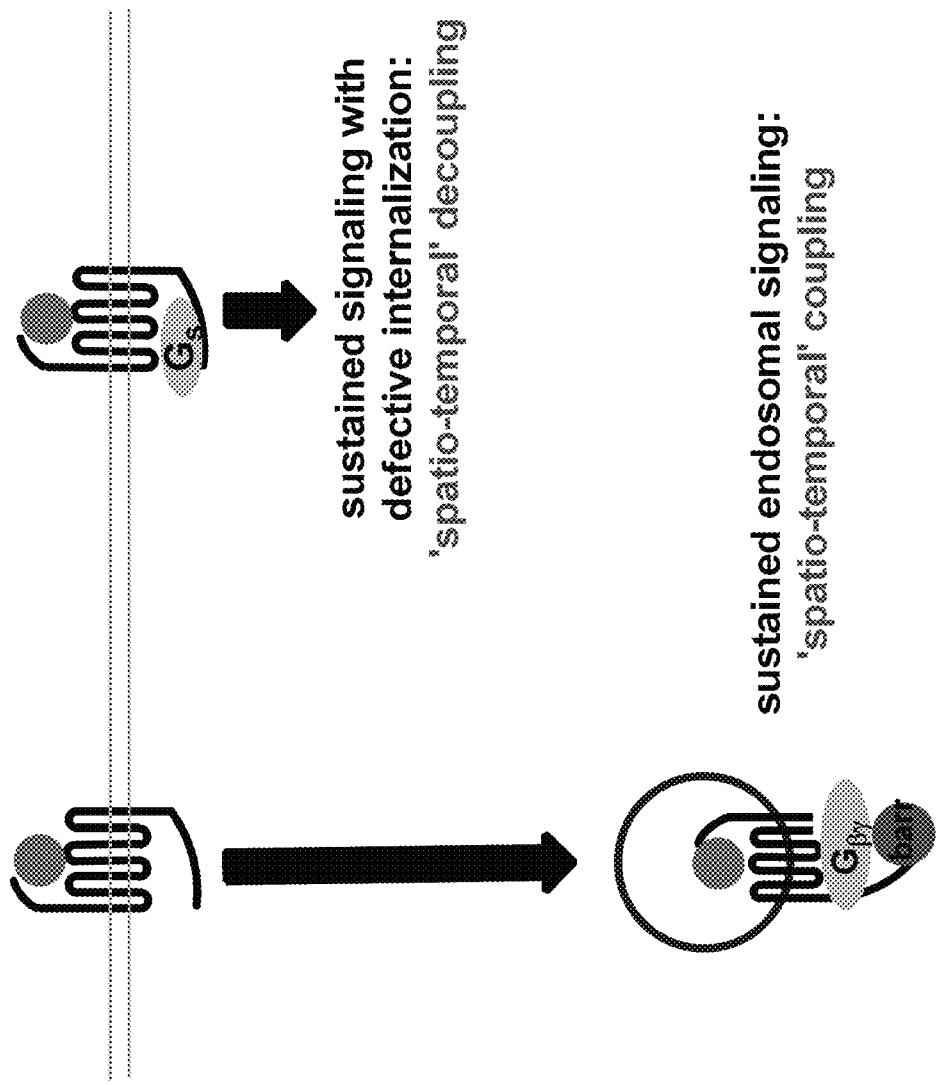
FIG. 9 is a schematic diagram presenting a possible explanation for the observed differences in signaling duration exhibited by different ligands.

Prolonged cAMP signaling of a PTHR1 agonist can cause both catabolic and anabolic effects. Intermittent PTH (1-34) administration is currently used to decouple bone resorption from bone formation. Spatial control of cAMP production within the cell, resulting from GPCR endocytosis, can be crucial in terms of downstream effects of receptor activation. See Irannejad et al. (2017) "Functional selectivity of GPCR-directed drug action through location bias," *Nature Chemical Biology* 13:799-806. The catabolic and anabolic effects of PTHR1 agonism might therefore be influenced by how effectively an agonist induces receptor endocytosis. This phenomenon can be evaluated using the novel ligands described herein. For example, despite its low efficiency in internalizing PTHR1, Ligand 10 can induce prolonged PTHR1 activation similar to PTH. Therefore, it is useful as a control ligand to study the potential spatial effect of prolonged endosomal PTHR1 activation. FIG. 9 presents a schematic representation of sustained endosomal signaling versus the proposed sustained signaling due to defective internalization.

The analogs are also useful as probes for pinpointing differences in ligand recognition by PTH1R and PTH2R.

'β scan' of the N-terminal portion of PTH(1-34)-NH$_2$. Implementing backbone-modification involves replacing one α-amino acid residue or more in an all-α sequence with a homologous β-amino acid residue. The β residue retains the original side chain (or a similar side chain) but contains an additional methylene in the backbone relative to the α residue that was replaced. β$^2$-homoamino acids, in which the side chain projects from the carbon adjacent to carbonyl have received little attention in the scientific literature because of diminished accessibility. As shown here, though, including β$^2$-homoamino acids is important for achieving agonist selectivity.

B-family GPCRs feature a large extracellular domain that binds to the C-terminal portion of a peptide agonist such as PTH(1-34); this portion of the agonist is usually α-helical in the bound state. The N-terminal portion of the agonist engages the transmembrane domain of the GPCR, but the receptor-bound conformations of most hormone N-terminal segments are unknown. In this work, it was hypothesized that α→β modifications in the N-terminal portion of PTH (1-34)-NH$_2$ would generate PTHR1 vs. PTHR2 selectivity. Thus, a β-scan of the first eight residues of this agonist was performed.

Many enantiopure β$^3$-homoamino acids with protecting groups necessary for solid-phase peptide synthesis are commercially available. In contrast, only a few protected β$^2$-homoamino acids can be purchased. This practical distinction has skewed the functional evaluation of peptides containing β-amino acid residues toward β$^3$ residues. Most prior work on peptides that contain α→β replacements (α/β-peptides) has focused on β$^3$ residues that maintain the configuration of L-α-amino acids, which means S for most β$^3$ residues but R in a few cases, such as β$^3$-hSer or β$^3$-hThr. Residues with this absolute stereochemistry, which we designate S* here [in other words, (R)-β$^3$-hSer is designated (S*)-β$^3$-hSer] can participate in right-handed α-helix-like secondary structures, as demonstrated crystallographically for numerous α/β-peptides containing 25-33% β residues distributed among L-α residues. In contrast, very little is known about the conformational or biological properties of α/β-peptides containing β$^2$ residues. Here, a three-part approach to the N-terminal β-scan of PTH(1-34)-NH$_2$ was undertaken in which each of the first eight residues was replaced by the (S*)-β$^3$, the (S*)-β$^2$ or the (R*)-β$^2$ homologue. For Met-8, the two β$^2$-homonorleucine (β$^2$-hNle) enantiomers were employed.

Tables 2 and 3 summarize the effects of single α→β replacements on PTHR1 and PTHR2 agonist activity.

TABLE 2

Tolerance pattern of β$^2$ and β$^3$ amino acids for PTHR1 and PTHR2 activation.

| Po-si-tion | PTHR1 Activation: Derivative EC$_{50}$/PTH EC$_{50}$ (0.38 nM) | | | PTHR2 Activation: Derivative EC$_{50}$/PTH EC$_{50}$ (0.97 nM) | | |
|---|---|---|---|---|---|---|
| | (R*)-β$^2$AA | (S*)-β$^2$AA | (S*)-β$^3$AA | (R*)-β$^2$AA | (S*)-β$^2$AA | (S*)-β$^3$AA |
| 1 | 0.92 | 1.34 | 0.71 | 6.86 | *1.78* | *0.63* |
| 2 | 11.76 | 18.34 | 1.45 | *0.24* | 5.43 | *0.92* |
| 3 | 78.84 | 13.08 | 21.82 | *** | 9.61 | *2.72* |
| 4 | 60.26 | 28.42 | 27.26 | *** | *** | 69.09 |
| 5 | 5.89 | 1.13 | 8.95 | *** | 17.23 | 10.92 |
| 6 | 20.61 | 1.11 | 22.24 | 59.70 | *2.25* | *0.21* |
| 7 | 0.95 | 1.24 | 2.21 | 47.64 | *0.28* | 40.28 |
| 8# | 1.05 | 1.00 | 55.24 | *** | 11.85 | *** |

Relative EC$_{50}$ values of PTH(1-34)-NH$_2$ analogues containing a single homologous α → β replacement within the first eight residues for PTHR1 and PTHR2 activation, as indicated by cAMP production, normalized to the EC$^{50}$ of PTH(1-34)-NH$_2$ itself.
Bold denotes tolerance of α → β, i.e., the corresponding α/β-peptide is a full PTHR1 agonist with EC50 < 2.5 times the EC50 of PTH(1-34)-NH$_2$.
*Bold italics* denotes tolerance of α → β replacement (analogous standard to that used for PTHR1).
*** denotes poor tolerance of β amino acid for PTHR2 activation.
Both β$^3$-hMet and β$^3$-hNle were tested at the 8$^{th}$ position; the value shown in table was the EC50 of β3-hMet (β$^3$-hNle is poorly tolerated at the 8$^{th}$ position for both PTHR1 and PTHR2 activation).

TABLE 3

EC$_{50}$ values of α/β PTH analogues for PTHR1 and PTHR2 activation.

| Position | EC50 (nM) of PTHR1 Activation | | | EC50 (nM) of PTHR2 Activation | | |
|---|---|---|---|---|---|---|
| | (R*)-β$^2$AA | (S*)-β$^2$AA | (S*)-β$^3$AA | (R*)-β$^2$AA | (S*)-β$^2$AA | (S*)-β$^3$AA |
| 1 | 0.35 ± 0.06 | 0.51 ± 0.07 | 0.27 ± 0.06 | 5.97 ± 1.21 | *1.55 ± 0.03* | *0.55 ± 0.16* |
| 2 | 4.47 ± 0.47 | 6.97 ± 1.00 | 0.55 ± 0.09 | *0.21 ± 0.03* | 4.72 ± 1.04 | *0.80 ± 0.14* |
| 3 | 29.96 ± 6.33 | 4.97 ± 0.72 | 8.29 ± 0.09 | >100 | 8.36 ± 0.69 | *2.37 ± 0.15* |
| 4 | 22.90 ± 1.89 | 10.80 ± 0.47 | 10.36 ± 1.87 | >1000 | >100 | 60.11 ± 9.82 |
| 5 | 2.24 ± 0.21 | 0.43 ± 0.06 | 3.40 ± 1.22 | >100 | 14.99 ± 3.70 | 9.50 1.67 |
| 6 | 7.83 ± 0.40 | 0.42 ± 0.07 | 8.45 ± 1.35 | 51.94 ± 8.82 | *1.96 ± 0.45* | *0.18 ± 0.02* |
| 7 | 0.36 ± 0.11 | 0.47 ± 0.14 | 0.84 ± 0.12 | 41.45 ± 5.18 | *0.24 ± 0.01* | 35.04 ± 2.84 |
| 8# | 0.40 ± 0.07 | 0.38 ± 0.07 | 20.99 ± 2.30 | >1000 | 10.31 ± 1.65 | >100 |

β$^2$-hNle was used instead of β$^2$-hMet.
Both β$^3$-hMet and β$^3$-hNle were tested at the 8$^{th}$ position; the value shown in table was the EC50 of β$^3$-hMet (β$^3$-hNle is poorly tolerated at the 8$^{th}$ position for both PTHR1 and PTHR2 activation).
Bold denotes tolerance of α → β, i.e., the corresponding α/β-peptide is a full PTHR1 agonist with EC50 < 2.5 times the EC50 of PTH(1-34)-NH$_2$.
*Bold italics* denotes tolerance of α → β replacement (analogous standard to that used for PTHR1).

The assays employ HEK-293 cells that have been engineered to express the appropriate receptor. GloSensor-based detection of cAMP provides a read-out of receptor activation. (Binkowski, B. F. et al. "A Luminescent Biosensor with Increased Dynamic Range for Intracellular cAMP." *Acs Chemical Biology* 6, 1193-1197 (2011).) Consistent with previous reports, PTH(1-34)-NH$_2$ is very active in both assays (EC$_{50}$=0.38 nM for PTHR1, and EC$_{50}$=0.87 nM for PTHR2). (Carter, P. H. et al. Actions of the Small Molecule Ligands SW106 and AH-3960 on the Type-1 Parathyroid Hormone Receptor. *Molecular Endocrinology* 29, 307-321 (2015).)

For PTHR1 activation, different patterns of substitution tolerance were observed among the α→β$^2$ and α→β$^3$ replacements. All three isomeric β residues were well-tolerated in place of Ser-1 or Leu-7, and none of the three was tolerated in place of Ser-3 or Glu-4. At the remaining positions, variable responses to α→β replacement were observed. Thus, for Val-2, the β$^3$ replacement has little effect on agonist potency, but both β$^2$ replacements cause significant declines in potency. For Ile-5, the β$^3$ and (R*)-β$^2$ replacements cause modest activity declines, but the (S*)-β$^2$ replacement matches PTH(1-34)-NH$_2$ in activity. Use of (S*)-β$^2$-hGln at position 6 has no effect on agonist activity, but placing either β$^3$-hGln or (R*)-β$^2$-hGln at this site causes a substantial activity decline. Both enantiomers of β$^2$-hNle are well-tolerated in place of Met-8, but use of either β$^3$-hMet or β$^3$-hNle at this position causes a substantial decline in activity. The overall trend among α→β$^3$ replacements is consistent with a previously reported β$^3$ scan of PTH (1-34)-NH$_2$.[28]

The PTHR2 assay displayed a greater sensitivity to α→β replacements than did the PTHR1 assay. For several single-β substitutions, the decline in agonist activity was so profound that an EC$_{50}$ value could not be determined. In contrast to the findings with PTHR1, there was no position among the first eight residues of PTH(1-34)-NH$_2$ at which all three isomeric α→β replacements were well tolerated. At position 1, the (S*)-β$^2$ and β$^3$ replacements had little effect on agonist potency, but the (R*)-β$^2$ replacement caused a modest decline. At position 2, the (S*)-β$^2$ replacement caused a modest activity decline, while the (R*)-β$^2$ and β$^3$ replacements were well tolerated. At the remaining sites, the (R*)-β$^2$ replacements were uniformly unfavorable in terms of agonist potency, while the impact of (S*)-β$^2$ replacements was quite variable, ranging from very disruptive (position 4) to well tolerated (positions 6 and 7). β$^3$ replacements at positions 3-8 of PTH(1-34)-NH$_2$ exerted variable effects on PTHR2 agonist activity as well, but the pattern differed from that manifested among the (S*)-β$^2$ replacements.

Enhanced selectivity via double α→β replacement. Based on the β scan results summarized in Tables 2 and 3, it appeared possible to design PTH(1-34)-NH$_2$ homologues containing α→β replacements at two sites in the N-terminal region that would display high selectivity for either PTHR1 activation or PTHR2 activation, in contrast to the potent activation of both receptors displayed by PTH(1-34)-NH$_2$ itself. As a PTHR1-selective candidate, we examined α/β-peptide 14 (SEQ. ID. NO: 14) which contains α→(R*)-β$^2$ replacements at positions 1 and 7. α/β-Peptide 15 (SEQ. ID. NO: 15) containing α→(R*)-β$^2$ replacement at position 2 and α→β$^3$ replacement at position 6, was evaluated as a PTHR2-selective candidate. The basis for these replacement choices is shown in Table 4.

TABLE 4

Tolerance pattern of β residues for PTHR1 and PTHR2 activation.

| | Tolerance Pattern of β AA | | |
|---|---|---|---|
| Position | (R*)-β$^2$AA | (S*)-β$^2$AA | (S*)-β$^3$AA |
| 1 | * | *# | *# |
| 2 | # | | *# |
| 3 | | | # |
| 4 | | | |
| 5 | | * | |
| 6 | | *# | # |
| 7 | * | *# | * |
| 8 | * | * | |

"*" denotes potent PTHR1-selective agonism;
"#" denotes potent PTHR2-selective agonism;
"*#" denotes potent agonism of both PTHR1 and PTHR2. Data represent mean ± s.e.m for ≥3 independent measurements.
β$^2$-hNle was used instead of β$^2$-hMet; both β$^3$-hMet and β$^3$-hNle were evaluated at the 8$^{th}$ position; the value shown is the EC$_{50}$ of β$^3$-hMet.

Results summarized in Table 5 show that for both 14 and 15, the two α→β replacements function synergistically.

TABLE 5

Signaling and binding properties of PTHR1- and PTHR2-selective α/β-peptide analogues of PTH(1-34)-NH$_2$. EC$_{50}$, E$_{max}$, R$^0$/RG IC$_{50}$ values for PTH(1-34)-NH$_2$, α/β-peptide 14, and α/β-peptide 15.

| | PTHR1 | | | | PTHR2 | | | |
|---|---|---|---|---|---|---|---|---|
| Peptide | EC$_{50}$ (nM) | E$_{max}$ | R$^0$-IC$_{50}$ (nM) | RG-IC$_{50}$ (nM) | EC$_{50}$ (nM) | E$_{max}$ | R$^0$-IC$_{50}$ (nM) | RG-IC$_{50}$ (nM) |
| PTH(1-34)-NH$_2$ | 0.22 ± 0.04 | 100 | 6.95 ± 0.81 | 0.34 ± 0.06 | 1.07 ± 0.14 | 100 | 0.96 ± 0.48 | 0.63 ± 0.23 |
| a/b-peptide 14 | 0.23 ± 0.04 | 100 ± 1 | 27.18 ± 7.22 | 0.13 ± 0.02 | ND | ND | 4.94 ± 0.81 | 0.04 ± 0.01 |
| a/b-peptide 15 | 22.90 ± 1.50 | 79 ± 6 | 5.25 ± 1.64 | 0.80 ± 0.08 | 0.13 ± 0.01 | 104 ± 2 | 0.64 ± 0.03 | 0.84 ± 0.19 |

Figure 10A:
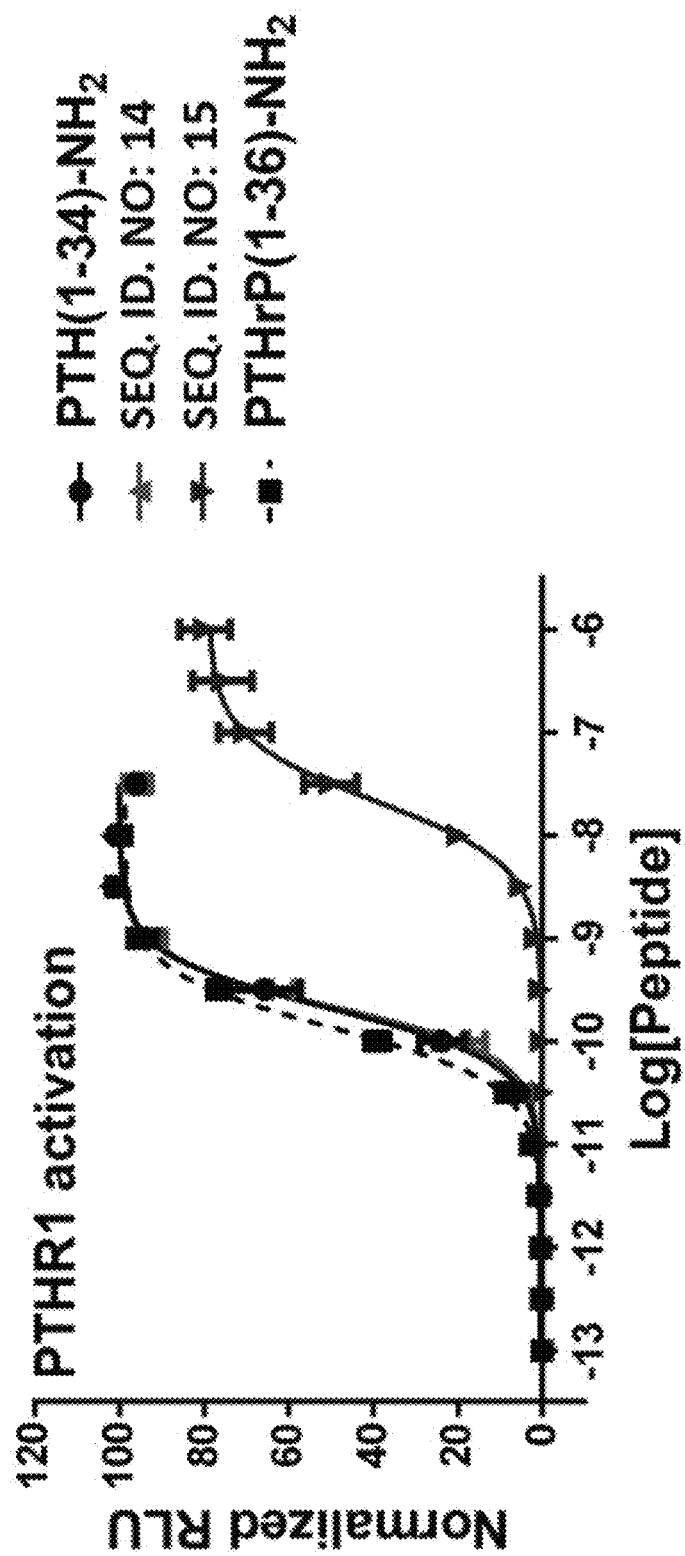
FIG. 10A is a dose-response curve of PTHR1 activation in HEK293 cells stably expressing PTHR1. Data represent mean±s.e.m from three independent measurements. Curves were fit to the data using a four-parameter sigmoidal dose-response equation.
Figure 10B:
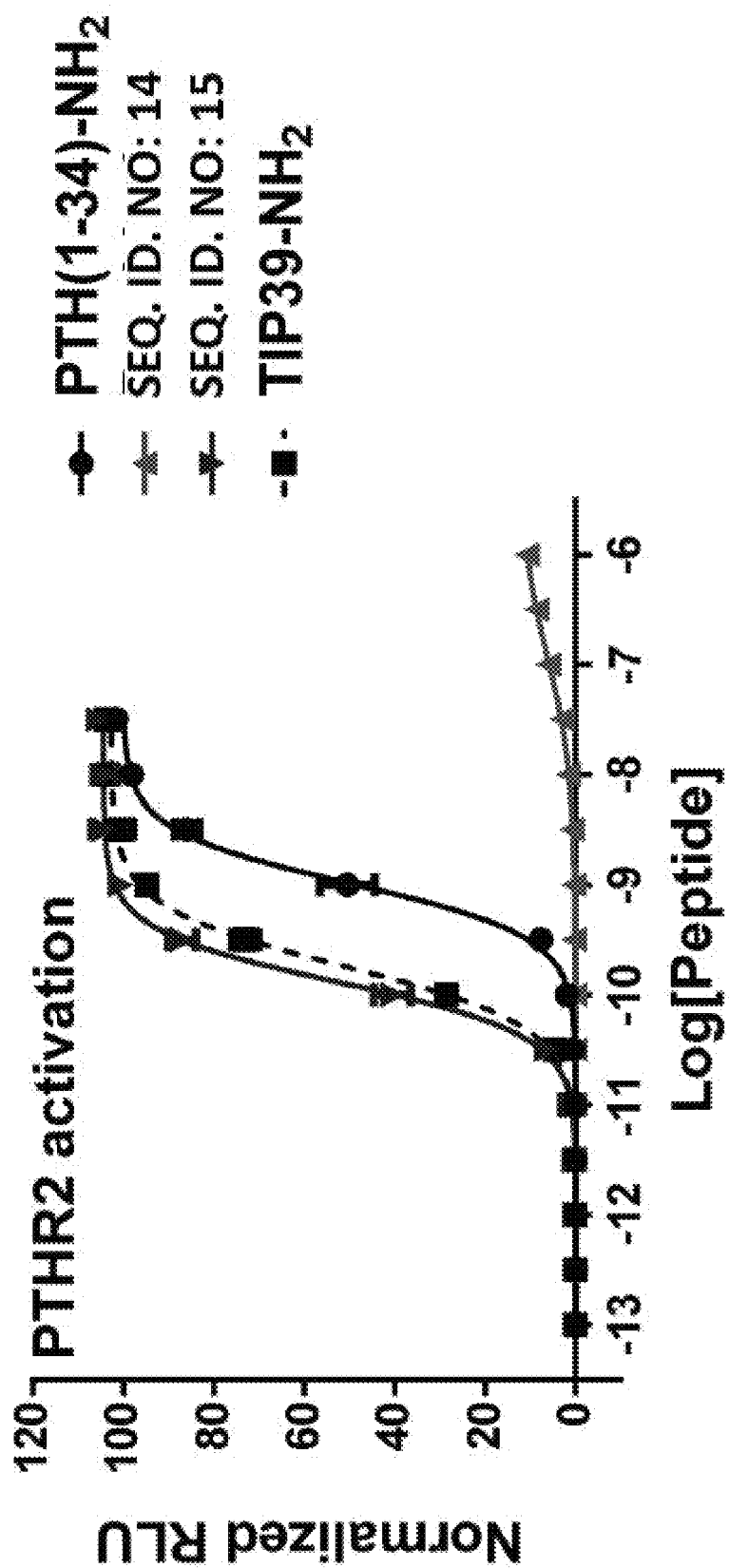
FIG. 10B is a dose-response curve of PTHR2 activation in HEK293 cells stably expressing PTHR2. For PTHR2 activation, data represent mean±s.e.m from four independent measurements. Binding data represent mean±s.e.m from three independent measurements. Curves were fit to the data using a four-parameter sigmoidal dose-response equation.

FIGS. 10A and 10B depict dose-response curves of PTHR1 activation (FIG. 10A) and PTHR2 activation (FIG. 10B) in HEK293 cells stably expressing PTHR1 or PTHR2. For PTHR1 activation and all the binding data, data represent mean±s.e.m from three independent measurements; For PTHR2 activation, data represent mean±s.e.m from four independent measurements. Curves were fit to the data using a four-parameter sigmoidal dose-response equation.

On one hand, neither replacement in 14, on its own, causes a diminution of PTHR1 agonist activity (Table 2), and implementing the two replacements simultaneously also does not cause an activity decline. On the other hand, each of the replacements in 14 leads to significant decline in PTHR2 agonist activity (~6-fold and ~40-fold), and the pairing generates an α/β-peptide that has almost no detectable activity for this receptor in this assay. For 15, the α→β replacements individually cause slight increases in agonist activity at PTHR2, and the combination of these backbone modifications leads to further potency enhancement relative to PTH(1-34)-NH$_2$. But, each of the replacements in α/β-peptide 15 causes a significant decline in PTHR1 agonist potency (~10-fold and ~20-fold), and the combination leads to a more substantial potency decline (~100-fold). Moreover, 15 reaches a maximum PTHR1 activation level that is only ~80% of the maximum achieved by PTH(1-34)-NH$_2$.

Binding to PTHR1 and PTHR2. The selective agonism displayed by α/β-peptides 14 and 15 relative to PTH(1-34)-NH$_2$ (SEQ. ID. NO: 16) could arise because of differences relative to PTH(1-34)-NH$_2$ in their affinities for PTHR1 and PTHR2, or because of differences in the abilities of 14 and 15 to activate each receptor upon binding. We conducted binding assays for PTHR1 and PTHR2 with these two PTH(1-34)-NH$_2$ analogues in an effort to distinguish these two possibilities. See Table 5. Two conformational states have been proposed for PTHR1 and for PTHR2, one that is G protein-dependent (RG) and another that is G protein-independent)(R$^0$.[5] Distinct assays are available for binding to the R$^0$ and RG states for each receptor. For both PTHR1 and PTHR2, α/β-peptide 14 has higher RG affinity and lower R$^0$ affinity than does PTH (1-34)-NH$_2$. In contrast, α/β-peptide 15 has lower RG affinity than does PTH(1-34)-NH$_2$ for both receptors, but 15 and PTH(1-34)-NH$_2$ are comparable in terms of R$^0$ affinity for both receptors. The PTHR1/PTHR2 R$^0$ affinity ratios are very similar for 14, 15 and PTH(1-34)-NH$_2$, and the PTHR1/PTHR2 RG affinity ratios vary only by approximately six-fold among these three agonists.

Figure 11:
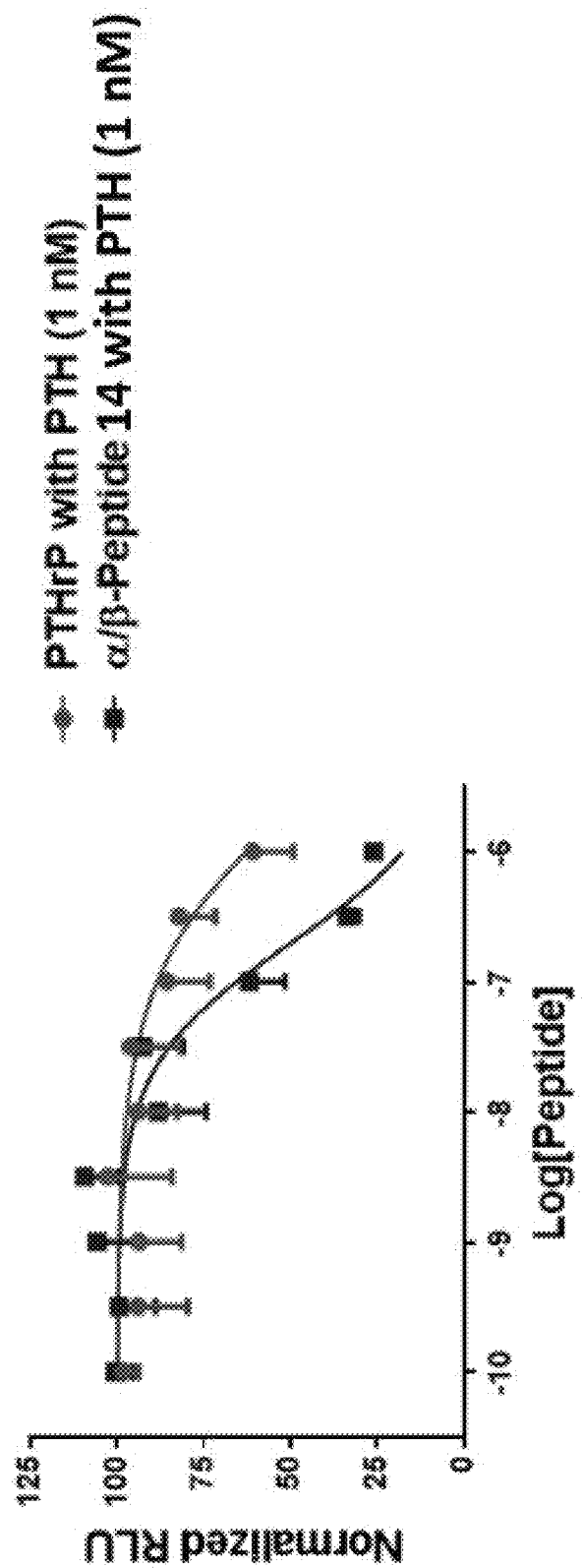
FIG. 11 is graph showing antagonistic effect of PTHrP (1-36)-NH$_2$ and α/β-peptide 14 on PTHR2 activation by PTH(1-34)-NH$_2$. Data points represent mean±s.e.m from four independent experiments. Curves were fit to the data using a four-parameter sigmoidal dose-response equation.

Collectively, these observations indicate that the selective agonism displayed by each of the α/β peptides arises mainly from selective receptor activation rather than from selective binding to one receptor or the other. Further evidence that a backbone-modified PTH(1-34)-NH$_2$ homologue can maintain affinity for a receptor despite loss of agonist activity was obtained from the observation that α/β-peptide 14 functions as an antagonist of PTHR2 activation by PTH(1-34)-NH$_2$. See FIG. 11. The conclusion that backbone-modified homologues of PTH(1-34)-NH$_2$ retain the ability to occupy the orthosteric site but are deficient in terms of inducing an active receptor conformation stands in contrast to previous analysis of naturally selective agonists PTHrP and TIP39, for which selectivity in receptor binding plays a major role in determining agonist selectivity. See Hoare, S. R. J., Clark, J. A. & Usdin, T. B. Molecular determinants of tuberoinfundibular peptide of 39 residues (TIP39) selectivity for the parathyroid hormone-2 (PTH2) receptor—N-terminal truncation of TIP39 reverses PTH2 receptor/PTH1 receptor binding selectivity. *Journal of Biological Chemistry* 275, 27274-27283 (2000) and Gardella, T. J., Luck, M. D., Jensen, G. S., Usdin, T. B. & Juppner, H. Converting parathyroid hormone-related peptide (PTHrP) into a potent PTH-2 receptor agonist. *Journal of Biological Chemistry* 271, 19888-19893 (1996).

Molecular basis of PTHR1 vs. PTHR2 selectivity. Previous receptor-mutation studies have identified sites within PTHR1 and PTHR2 that play critical roles in determining peptide agonist selectivity. (Bergwitz, C., Jusseaume, S. A., Luck, M. D., Juppner, H. & Gardella, T. J. Residues in the membrane-spanning and extracellular loop regions of the parathyroid hormone (PTH)-2 receptor determine signaling selectivity for PTH and PTH-related peptide. *Journal of Biological Chemistry* 272, 28861-28868 (1997).) For example, PTHrP (1-36)-NH$_2$ is a potent agonist of PTHR1 and a very weak agonist of PTHR2; however, modifications at three sites in PTHR2, based on residues found at analogous sites in PTHR1, rescue the agonist activity of PTHrP (1-36)-NH$_2$. Specifically, any of three modifications to the PTHR2 sequence, (i) replacement of residues 199-20 at the N-terminal side of extracellular loop 1 (ECL1) of PTHR2 with the corresponding segment of PTHR1, (ii) mutation of I244 to L, or (iii) mutation of Y318 to I, generates a PTHR2 variant that is much more susceptible to activation by PTHrP (1-36)-NH$_2$ relative to wide-type PTHR2 (data not shown). Evaluation of α/β-peptide 14 with this panel of three PTHR2 variants yields an activity profile that is distinct from the activity profile observed with PTHrP(1-36)-NH$_2$. At the level of receptor expression required to detect significant activity rescue for 100 nM PTHrP(1-36)-NH$_2$ at the three mutant receptors, substantial activity at wild-type PTHR2 is observed for 100 nM α/β-peptide 14. Significant increases in agonist activity are observed for two of the PTHR2 variants relative to wild-type receptor (ECL1 chimera and Y318I), but a decrease is evident relative to wild-type receptor for the third PTHR2 variant, I244L. Detailed interpretation of these differences is not possible in the absence of atomic-resolution structural data for PTHR1 or PTHR2, but the distinct response profiles of PTHrP(1-36)-NH$_2$ and α/β-peptide 14 to this set of receptor variants, particularly I244L, suggest that the molecular determinants underlying the PTHR1 vs. PTHR2 selectivity are at least partially different between PTHrP(1-36)-NH$_2$ and α/β-peptide 14.

Reciprocal point mutations of PTHR1 were investigated to see if they would enhance the signaling activity of PTHR2-selective agonists. TIP39-NH$_2$ does not activate wild-type PTHR1 and appears to be a very weak agonist of mutants PTHR1-L289I and PTHR1-I363Y (data not shown). α/β-Peptide 15 deviates partially from this pattern in that PTHR1-I363Y is even less susceptible to activation by 15 than is wild-type PTHR1. Overall, the observations with receptor variants suggest that the response of PTHR1 and PTHR2 to agonists that are selective by virtue of side chain identity (such as PTHrP (1-36)-NH$_2$ or TIP39-NH$_2$) involves a set of contact residues on the receptor that is partially distinct from those that mediate the response to agonists that are selective by virtue of backbone modification (such as α/β-peptides 14 and 15).

Duration of activation for PTHR1 and PTHR2. To assess the duration of PTHR1 and PTHR2 activation induced by α/β-peptides 14 and 15, the time course of cAMP production by each receptor was examined after stimulation with an agonist and subsequent washing of the cells to remove unbound peptide (wash-out assay). PTH(1-34)-NH$_2$ and the naturally selective agonists PTHrP(1-36)-NH$_2$ and TIP39-NH$_2$ were used as controls. During the initial "ligand-on" phase, cells stably expressing PTHR1 or PTHR2 were stimulated with an agonist concentration corresponding to ~EC$_{80}$; the medium contained D-luciferin. The luminescence emission caused by cAMP production was monitored until each agonist reached maximum response (E$_{max}$; ~14 min in each case), at which point unbound peptide was washed away. After the addition of fresh medium containing D-luciferin, the luminescence decay is measured. The area under the "ligand-off" curve (AUC) reflects the duration of signaling, which may be related to residence time of the agonist on the receptor but could have other origins at the molecular level. At PTHR1, the selective agonists α/β-peptide 14 and PTHrP(1-36)-NH$_2$ lead to more transient signaling (smaller AUC) than does PTH(1-34)-NH$_2$. See Table S1a.[6] At PTHR2, the selective agonists α/β-peptide 15 and TIP39-NH$_2$ induce more prolonged signaling than does PTH(1-34)-NH$_2$. See Table S1b.[7]

Data represent mean±s.e.m from 10 independent experiments. b. PTHR2 signaling durations of PTH(1-34)-NH$_2$, TIP39-NH$_2$, and α/β-peptide 2. Data represent mean±s.e.m from 11 independent experiments

TABLE 6

PTHR1 signaling durations of PTH(1-34)-NH$_2$, PTHrP(1-36)-NH$_2$, and α/β-peptide 14.

| Peptide | Normalized ligand-on E$_{max}$ | Normalized ligand-off AUC |
|---|---|---|
| PTH(1-34)-NH$_2$ | 100 | 100 |
| PTHrP(1-36)-NH$_2$ | 102 ± 1 | 55 ± 2 |
| α/β-peptide 14 | 99 ± 2 | 68 ± 3 |

Data represent mean ± s.e.m from 10 independent experiments.

TABLE 7

PTHR2 signaling durations of PTH(1-34)-NH$_2$, TIP39-NH$_2$, and α/β-peptide 2.

| Peptide | Normalized ligand-on E$_{max}$ | Normalized ligand-off AUC |
|---|---|---|
| PTH(1-34)-NH$_2$ | 100 | 100 |
| TIP39-NH$_2$ | 99 ± 1 | 226 ± 22 |
| α/β-peptide 1 | 103 ± 1 | 197 ± 16 |

Data represent mean ± s.e.m from 11 independent experiments.

EC50 data for the complete series of systematic substitutions is shown in Table 8

TABLE 8

Agonist activity toward hPTHR1 and hPTHR2

| Polypeptide | PTHR1 EC50 (nM) | PTHR1 EC50 (nM) |
|---|---|---|
| PTH: SVSEIQLMHNLGKHLNSMERVEWLRKKLQDVHNF—NH$_2$ (SEQ. ID. NO: 16) | 0.38 ± 0.04 | 0.87 ± 0.09 |
| SVSEIQLMHNLGKHLNSMERVEWLRKKLQDVHNF—NH$_2$ (SEQ. ID. NO: 22) | 0.35 ± 0.06 | 5.97 ± 1.21 |
| SVSEIQLMHNLGKHLNSMERVEWLRKKLQDVHNF—NH$_2$ (SEQ. ID. NO: 23) | 4.47 ± 0.47 | 0.21 ± 0.03 |
| SVSEIQLMHNLGKHLNSMERVEWLRKKLQDVHNF—NH$_2$ (SEQ. ID. NO: 24) | 29.96 ± 6.33 | >100 |
| SVSEIQLMHNLGKHLNSMERVEWLRKKLQDVHNF—NH$_2$ (SEQ. ID. NO: 25) | 22.90 ± 1.89 | >1000 |
| SVSEIQLMHNLGKHLNSMERVEWLRKKLQDVHNF—NH$_2$ (SEQ. ID. NO: 26) | 2.24 ± 0.21 | >100 |
| SVSEIQLMHNLGKHLNSMERVEWLRKKLQDVHNF—NH$_2$ (SEQ. ID. NO: 27) | 7.83 ± 0.40 | 51.94 ± 8.82 |
| SVSEIQLMHNLGKHLNSMERVEWLRKKLQDVHNF—NH$_2$ (SEQ. ID. NO: 28) | 0.36 ± 0.11 | 41.45 ± 5.18 |
| SVSEIQL$^N$LHNLGKHLNSMERVEWLRKKLQDVHNF—NH$_2$ (SEQ. ID. NO: 29) | 0.40 ± 0.07 | >1000 |

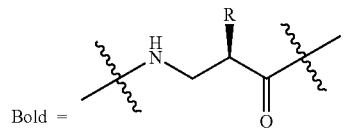

Bold =

| | | |
|---|---|---|
| SVSEIQLMHNLGKHLNSMERVEWLRKKLQDVHNF—NH$_2$ (SEQ. ID. NO: 30) | 1.55 ± 0.30 | 1.55 ± 0.30 |
| SVSEIQLMHNLGKHLNSMERVEWLRKKLQDVHNF—NH$_2$ (SEQ. ID. NO: 31) | 4.72 ± 1.04 | 4.72 ± 1.04 |
| SVSEIQLMHNLGKHLNSMERVEWLRKKLQDVHNF—NH$_2$ (SEQ. ID. NO: 32) | 8.36 ± 0.69 | 8.36 ± 0.69 |
| SVSEIQLMHNLGKHLNSMERVEWLRKKLQDVHNF—NH$_2$ (SEQ. ID. NO: 33) | >100 | >100 |
| SVSEIQLMHNLGKHLNSMERVEWLRKKLQDVHNF—NH$_2$ (SEQ. ID. NO: 34) | 14.99 ± 3.70 | 14.99 ± 3.70 |
| SVSEIQLMHNLGKHLNSMERVEWLRKKLQDVHNF—NH$_2$ (SEQ. ID. NO: 35) | 1.96 ± 0.45 | 1.96 ± 0.45 |
| SVSEIQLMHNLGKHLNSMERVEWLRKKLQDVHNF—NH$_2$ (SEQ. ID. NO: 36) | 0.24 ± 0.01 | 0.24 ± 0.01 |
| SVSEIQL$^N$LHNLGKHLNSMERVEWLRKKLQDVHNF—NH$_2$ (SEQ. ID. NO: 37) | 10.3 ± 1.65 | 10.31 ± 1.65 |

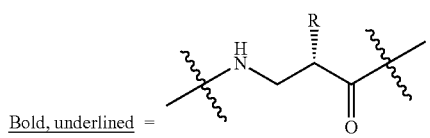

Bold, underlined =

| | | |
|---|---|---|
| <u>S</u>VSEIQLMHNLGKHLNSMERVEWLRKKLQDVHNF—NH$_2$ (SEQ. ID. NO: 38) | 0.27 ± 0.06 | 0.55 ± 0.16 |
| S<u>V</u>SEIQLMHNLGKHLNSMERVEWLRKKLQDVHNF—NH$_2$ (SEQ. ID. NO: 39) | 0.55 ± 0.09 | 0.80 ± 0.14 |

TABLE 8-continued

Agonist activity toward hPTHR1 and hPTHR2

| Polypeptide | PTHR1 EC50 (nM) | PTHR1 EC50 (nM) |
|---|---|---|
| SVSSEIQLMHNLGKHLNSMERVEWLRKKLQDVHNF—NH$_2$ (SEQ. ID. NO: 40) | 8.29 ± 0.09 | 2.37 ± 0.15 |
| SVSEIQLMHNLGKHLNSMERVEWLRKKLQDVHNF—NH$_2$ (SEQ. ID. NO: 41) | 10.36 ± 1.87 | 60.11 ± 9.82 |
| SVSEIQLMHNLGKHLNSMERVEWLRKKLQDVHNF—NH$_2$ (SEQ. ID. NO: 42) | 3.40 ± 1.22 | 9.50 ± 1.67 |
| SVSEIQLMHNLGKHLNSMERVEWLRKKLQDVHNF—NH$_2$ (SEQ. ID. NO: 43) | 8.45 ± 1.35 | 0.18 ± 0.02 |
| SVSEIQLMHNLGKHLNSMERVEWLRKKLQDVHNF—NH$_2$ (SEQ. ID. NO: 44) | 0.84 ± 0.12 | 35.04 ± 2.84 |
| SVSEIQLMHNLGKHLNSMERVEWLRKKLQDVHNF—NH$_2$ (SEQ. ID. NO: 45) | 20.99 ± 2.30 | >100 |

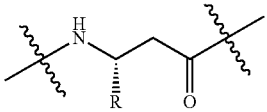

Bold, double-underline =

Nutritional Compositions:

The present disclosure includes nutritional compositions. Such compositions include any food or preparation for human consumption (including for enteral or parenteral consumption) which when taken into the body (a) serve to nourish or build up tissues or supply energy and/or (b) maintain, restore or support adequate nutritional status or metabolic function.

The nutritional composition comprises at least one PTH analog as described herein and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany hyperglycemic metabolic conditions.

Examples of macronutrients which may be added to the composition include but are not limited to edible fats, carbohydrates and proteins. Examples of such edible fats include but are not limited to coconut oil, soy oil, and mono- and diglycerides. Examples of such carbohydrates include but are not limited to glucose, edible lactose and hydrolyzed starch. Additionally, examples of proteins which may be utilized in the nutritional composition include but are not limited to soy proteins, electrodialysed whey, electrodialysed skim milk, milk whey, or the hydrolysates of these proteins.

With respect to vitamins and minerals, the following may be added to the nutritional compositions described herein: calcium, phosphorus, potassium, sodium, chloride, magnesium, manganese, iron, copper, zinc, selenium, iodine, and Vitamins A, E, D, C, and the B complex. Other such vitamins and minerals may also be added.

Examples of nutritional compositions disclosed herein include but are not limited to infant formulas, dietary supplements, dietary substitutes, and rehydration compositions. Nutritional compositions of particular interest include but are not limited to those utilized for enteral and parenteral supplementation for infants, specialist infant formulas, supplements for the elderly, and supplements for those with hyperglycemia.

The nutritional composition of the present invention may also be added to food even when supplementation of the diet is not required. For example, the composition may be added to food of any type including but not limited to margarines, modified butters, cheeses, milk, yoghurt, chocolate, candy, snacks, salad oils, cooking oils, cooking fats, meats, fish and beverages.

In a preferred version, the nutritional composition is an enteral nutritional product, more preferably, an adult or pediatric enteral nutritional product. This composition may be administered to adults or children experiencing stress or having specialized needs due to chronic or acute disease states. The composition may comprise, in addition to PTH (1-34) analogs described herein, macronutrients, vitamins and minerals as described above. The macronutrients may be present in amounts equivalent to those present in human milk or on an energy basis, i.e., on a per calorie basis.

Methods for formulating liquid or solid enteral and parenteral nutritional formulas are well known in the art. An enteral formula, for example, may be sterilized and subsequently utilized on a ready-to-feed (RTF) basis or stored in a concentrated liquid or powder. The powder can be prepared by spray drying the formula prepared as indicated above, and reconstituting it by rehydrating the concentrate. Adult and pediatric nutritional formulas are well known in the art and are commercially available (e.g., Similac®-brand and Ensure®-brand formulas from from Ross Products Division, Abbott Laboratories, Columbus, Ohio). A PTH(1-34) analog produced in accordance with the present disclosure may be added to commercial formulas of this type.

The energy density of the nutritional compositions in liquid form may range from about 0.6 Kcal to about 3 Kcal per ml. When in solid or powdered form, the nutritional supplements may contain from about 1.2 to more than 9 Kcals per gram, preferably about 3 to 7 Kcals per gm. In general, the osmolality of a liquid product should be less than 700 mOsm and, more preferably, less than 660 mOsm.

Pharmaceutical Compositions:

Also disclosed herein are pharmaceutical compositions comprising one or more of the PTH analogs or a pharmaceutically suitable salt thereof as described herein. More specifically, the pharmaceutical composition may comprise one or more of the PTH analogs as well as a standard, well-known, non-toxic pharmaceutically suitable carrier, adjuvant or vehicle such as, for example, phosphate buffered saline, water, ethanol, polyols, vegetable oils, a wetting agent or an emulsion such as a water/oil emulsion. The composition may be in either a liquid, solid or semi-solid form. For example, the composition may be in the form of a tablet, capsule, ingestible liquid or powder, injectible, suppository, or topical ointment or cream. Proper fluidity can be maintained, for example, by maintaining appropriate particle size in the case of dispersions and by the use of surfactants. It may also be desirable to include isotonic agents, for example, sugars, sodium chloride, and the like. Besides such inert diluents, the composition may also include adjuvants, such as wetting agents, emulsifying and suspending agents, sweetening agents, flavoring agents, perfuming agents, and the like.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art of pharmacy. For example, PTH analogs produced as described herein can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant PTH analog.

For intravenous administration, the analogs may be incorporated into commercial formulations such as Intralipid©-brand fat emulsions for intravenous injection. ("Intralipid" is a registered trademark of Fresenius Kabi A B, Uppsalla, Sweden.) Where desired, the individual components of the formulations may be provided individually, in kit form, for single or multiple use. A typical intravenous dosage of a representative PTH analog as described herein is from about 0.1 mg to 100 mg daily and is preferably from 0.5 mg to 20 mg daily. Dosages above and below these stated ranges are specifically within the scope of the claims.

Possible routes of administration of the pharmaceutical compositions include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant. The route of administration will, of course, depend upon the desired effect and the medical stated of the subject being treated. The dosage of the composition to be administered to the patient may be determined by one of ordinary skill in the art and depends upon various factors such as weight of the patient, age of the patient, immune status of the patient, etc., and is ultimately at the discretion of the medical professional administering the treatment.

With respect to form, the composition may be, for example, a solution, a dispersion, a suspension, an emulsion or a sterile powder which is then reconstituted. The composition may be administered in a single daily dose or multiple doses.

The present disclosure also includes treating hypoparathyroid disorders in mammals, including humans, by administering an anti-hypoparathyroid-effective and/or PTHR agonist-effective amount of one or more the PTH analogs described herein. In particular, the compositions of the present invention may be used to treat hypoparathyroid conditions of any and all description.

It should be noted that the above-described pharmaceutical and nutritional compositions may be utilized in connection with non-human animals, both domestic and non-domestic, as well as humans.

Peptide Synthesis and Purification:

Peptides were synthesized as C-terminal amides on NovaPEG rink amide resin (EMD-Millipore, Billerica, Mass.) using previously reported microwave-assisted solid-phase conditions based on Fmoc protection of main chain amino groups.[31] Briefly, protected amino acids were activated with 2-(1H-benzotriazole-1-yl)-1,1,3,3-tetramethyluronium hexafluorophosphate (HBTU) and N-hydroxybenzotriazole (HOBt) in the presence of N,N-diisopropylethylamine (DIEA). The growing peptide chain was deprotected using 20% piperdine in DMF. Protected $\beta^3$-homoamino acids were purchased from PepTech Corporation (Bedford, Mass.).

After synthesis, the peptides were cleaved from the resin and side chains were deprotected using reagent K (82.5% TFA, 5% phenol, 5% $H_2O$, 5% thioanisole, 2.5% ethanedithiol)[31] for two hours. The TFA solution was dripped into cold diethyl ether to precipitate the deprotected peptide. Peptides were purified on a prep-C18 column using reverse phase-HPLC. Purity was assessed by analytical RP-HPLC (solvent A: 0.1% TFA in water, solvent B: 0.1% TFA in acetonitrile, C18 analytical column (4.6×250 mm), flow rate 1 mL/min, gradient 10-60% B solvent over 50 minutes). Masses were measured by MALDI-TOF-MS.

Protease Stability:

An HPLC assay was used to assess proteolytic stability.[30, 32] Peptide concentration was determined by UV-Vis spectroscopy (calculated from the UV-vis absorption at 280 nm, $\varepsilon_{280\ nm}$=5,690 $M^{-1}$ $cm^{-1}$ for all peptides except D6 and D7, $\varepsilon_{280\ nm}$=11,380 $M^{-1}$ $cm^{-1}$ based on an extinction coefficient for the tryptophan sidechain chromophore of 5,690 $M^{-1}$ $cm^{-1}$).[33] Peptide stock solutions were prepared in degassed water to a concentration of 200 μM. Sequencing-grade trypsin from bovine pancreas was purchased from Sigma Aldrich (St. Louis, Mo.) and prepared to a stock concentration of 100 m/mL in 1 mM HCl. The protease reaction was carried out in 0.6 mL Eppendorf tubes at room temperature. The reaction solution was prepared by combining 40 μL of 200 μM peptide (final concentration 40 μM), 20 μL of 10×TBS pH 8.5 (final concentration 15 mM Tris, 150 mM NaCl, or 1×TBS), 130 μL of water, and 10 μL of 100 m/mL protease (added last, final concentration 5 m/mL, in a total volume of 200 μL). Each proteolysis experiment was run in duplicate. Following addition of protease, the reaction was timed and quenched by combining a 50 μL aliquot of the proteolysis mixture with 50 μL of 0.1% trifluoroacetic acid in acetonitrile. A portion (75 μL) of the quenched reaction mixture was injected onto an analytical RP-HPLC (see peptide synthesis and purification section above), and peaks were analyzed. The time course of peptide degradation was experimentally determined by integrating the area of the peak corresponding to the non-hydrolyzed peptide in a series of HPLC traces, with duplicate proteolysis reactions being used to generate error bars corresponding to the standard deviation. The final 50 μL of the reaction solution was used to acquire MALDI-TOF mass spectrometry data for identification of peptide fragments resulting from proteolysis. Proteolysis was observed at all predicted trypsin cut sites for PTH(1-34). Shown in FIGS. 5A, 5B, and 5C are time course data for peptide degradation. Exponential decay curves and half-life values were generated using GraphPad Prism version 5.0 (GraphPad Software, La Jolla, Calif.).

Binding and cAMP Dose Response:

Reported $IC_{50}$ and $EC_{50}$ values are the average of ≥4 independent measurements. Each assay comprises ≥7 data points (different concentrations) per α/β-peptide, with each data point representing the average from duplicate wells. Binding to the RG and $R^0$ conformations of the human or rat PTHR-1 was assessed by competition assays performed in 96-well plates by using membranes from transiently transfected COS-7 cells as previously described.[6,7] In brief, binding to $R^0$ was assessed by using $^{125}$I-PTH(1-34) as tracer radio-ligand and including GTPγS in the reaction (1×10$^{-5}$ M). Binding to RG was assessed by using membranes containing a high-affinity, negative-dominant $G_\alpha S$ subunit ($G_\alpha S$ ND)[15], and $^{125}$I-M-PTH(1-15)[6] as tracer radio-ligand.

cAMP signaling was assessed using HEK-293-derived cell lines that stably express the GloSensor™-brand cAMP reporter (Promega Corp.) along with either the WT human PTHR-1 (GP-2.3 cells) or WT rat PTHR-1 (GR-35 cells). For cAMP dose-response assays, monolayers of confluent HEK 293 cells were pre-incubated with buffer containing d-luciferin (0.5 mM) in 96 well plates at room temperature until a stable baseline level of luminescence was established (30 min). Varying concentrations of agonist were then added, and the time course of luminescence response was recorded using a Perkin Elmer plate reader following α/β-peptide addition. The maximal luminescence response (observed 12-16 min after ligand addition) was used for generating dose response curves.

"Washout" Assays:

The duration of PTH analog stimulated cAMP response following removal of the solution containing dissolved peptide from the confluent HEK293 cell monolayers has been shown to be predictive of the duration of in vivo calcemic responses in mice.[8] This parameter of in vitro PTH analog performance shows strong positive correlation with $R^0$ binding affinity (high $R^0$ binding affinity correlates with prolonged cAMP signaling following washout). Washout assays were carried out for PTH(1-34), LA-PTH, and Ligands 8, 10, 12, and 100 to assess the contribution of altered $R^0$ binding affinity to the duration of calcemic responses observed in vivo. M-PTH(1-34) (data not shown), a sidechain-altered PTH analog that has previously been shown to induce prolonged responses following washout and prolonged calcemic response in vivo with native-like bioavailability, was included as a control. HEK293 cell monolayers expressing rat PTHR-1 (GR35 cells) were treated with ligand in for 14 minutes. This buffer was then discarded, and the cell monolayer was rinsed (2×). Buffer containing luciferin was introduced for 120 minutes. Luminescence response was recorded before and after washout, with luminescence readings recorded every 2 minutes. The area under the curve (AUC) for luminescence response curve was determined using GraphPad Prism.

In Vivo Pharmacology: Calcemic Response:

PTH(1-34) causes a transient rise in the blood concentration of $Ca^{2+}$, which peaks after about one hour.[8] Okazaki et al. have proposed that the calcemic effect duration resulting from injection of a PTHR-1 agonist is controlled, at least in part, by affinity for the $R^0$ state of the receptor.[8] According to this hypothesis, agonists with high $R^0$ affinity can remain bound to the receptor through multiple cycles of $G_\alpha$ binding and release, which should induce prolonged signaling.[7] The pathways by which PTH is removed from circulation have not been fully elucidated, but enzymatic degradation probably contributes to the rapid disappearance of PTH(1-34) in vivo.[20]

To evaluate calcemic response, mice (C57BL/6, male, age 9-12 weeks) are treated in accordance with the ethical guidelines adopted by Massachusetts General Hospital. Mice (n=5 per compound) and are injected subcutaneously with vehicle (10 mM citric acid/150 mM NaCl/0.05% Tween-80, pH 5.0) or vehicle containing PTH(1-34) or one of the ligands disclosed herein at a dose of 20 nmol/kg body weight. Blood is withdrawn just prior to injection (t=0) or at times thereafter. Tail vein blood is collected and immediately used for analysis. Blood $Ca^{2+}$ concentration is measured with a Chiron Diagnostics model 634 $Ca^{2+}$/pH analyzer.

In Vivo Pharmacokinetics:

Blood content of the ligands described herein analog is assessed in plasma from mice injected with vehicle or vehicle containing a ligand as described herein at a dose of 20 nmol/kg body weight in an experiment performed separately from the calcemic response assays described above. Blood is withdrawn just prior to injection (t=0) or at times thereafter. Tail vein blood is collected and treated with protease inhibitors (aprotinin, leupeptin, EDTA), centrifuged to remove blood cells, mixed with cAMP response assay buffer, and administered to GP2.3 cells. The raw luminescence readouts recorded in this assay are converted to blood peptide concentrations through use of a standard curve relating luminescence response to known peptide concentrations under identical assay conditions.

Data Calculations:

Data were processed by using the Microsoft Excel and GraphPad Prism 4.0 software packages. Data from binding and cAMP dose—response assays were analyzed using a sigmoidal dose—response model with variable slope. Washout responses were assessed by quantifying the area under the luminescence response curve (AUC) following washout. Post-washout AUC was normalized by dividing the post-washout AUC by the pre-washout AUC. Paired data sets were statistically compared by using Student's t test (two-tailed) assuming unequal variances for the two sets.

REFERENCES CITED

The following documents are incorporated herein by reference.

1. Rajagopal, S., Rajagopal, K. & Lefkowitz, R. J. Teaching old receptors new tricks: biasing seven-transmembrane receptors. *Nat. Rev. Drug Discovery* 9, 373-386 (2010).
2. Kenakin, T. & Christopoulos, A. Signaling bias in new drug discovery: detection, quantification and therapeutic impact. *Nat. Rev. Drug Discovery* 12, 205 (2013).
3. Rajagopal, S. et al. Quantifying Ligand Bias at Seven-Transmembrane Receptors. *Mol. Pharmacol.* 80, 367-377 (2011).
4. Venkatakrishnan, A. J. et al. Molecular signatures of G-protein-coupled receptors. *Nature* 494, 185-194 (2013).
5. Hoare, S. R. J., Gardella, T. J. & Usdin, T. B. Evaluating the signal transduction mechanism of the parathyroid hormone 1 receptor—Effect of receptor-G-protein interaction on the ligand binding mechanism and receptor conformation. *J. Biol. Chem.* 276, 7741-7753 (2001).
6. Dean, T. et al. Mechanisms of ligand binding to the parathyroid hormone (PTH)/PTH-related protein receptor: Selectivity of a modified PTH(1-15) Radioligand for Gα$_s$-coupled receptor conformations. *Mol. Endocrinol.* 20, 931-943 (2006).
7. Dean, T., Vilardaga, J. P., Potts, J. T. & Gardella, T. J. Altered selectivity of parathyroid hormone (PTH) and PTH-Related protein (PTHrP) for distinct conformations of the PTH/PTHrP receptor. *Mol. Endocrinol.* 22, 156-166 (2008).
8. Okazaki, M. et al. Prolonged signaling at the parathyroid hormone receptor by peptide ligands targeted to a specific receptor conformation. *Proc. Natl. Acad. Sci. U.S.A.* 105, 16525-16530 (2008).
9. Vilardaga, J. P., Romero, G., Friedman, P. A. & Gardella, T. J. Molecular basis of parathyroid hormone receptor signaling and trafficking: a family B GPCR paradigm. *Cell. Mol. Life Sci.* 68, 1-13 (2011).
10. Feinstein, T. N. et al. Retromer terminates the generation of cAMP by internalized PTH receptors. *Nat. Chem. Biol.* 7, 278-284 (2011).
11. Neer, R. M. et al. Effect of parathyroid hormone (1-34) on fractures and bone mineral density in postmenopausal women with osteoporosis. *N. Engl. J. Med.* 344, 1434-1441 (2001).
12. Pioszak, A. A. & Xu, H. E. Molecular recognition of parathyroid hormone by its G protein-coupled receptor. *Proc. Natl. Acad. Sci. U.S.A.* 105, 5034-5039 (2008).
13. Boersma, M. D. et al. Evaluation of Diverse alpha/beta-Backbone Patterns for Functional α-Helix Mimicry: Analogs of the Bim BH3 Domain. *J. Am. Chem. Soc.* 134, 315-323 (2012).
14. Hoare, S. R. J., De Vries, G. & Usdin, T. B. Measurement of agonist and antagonist ligand-binding parameters at the human parathyroid hormone type 1 receptor: Evaluation of receptor states and modulation by guanine nucleotide. *J. Pharmacol. Exp. Ther.* 289, 1323-1333 (1999).
15. Berlot, C. H. A highly effective dominant negative α$_s$ construct containing mutations that affect distinct functions inhibits multiple G$_s$-coupled receptor signaling pathways. *J. Biol. Chem.* 277, 21080-21085 (2002).
16. Binkowski, B. F. et al. A Luminescent Biosensor with Increased Dynamic Range for Intracellular cAMP. *ACS Chem. Biol.* 6, 1193-1197 (2011).
17. Piserchio, A., Shimizu, N., Gardella, T. J. & Mierke, D. F. Residue 19 of the parathyroid hormone: Structural consequences. *Biochemistry* 41, 13217-13223 (2002).
18. Schievano, E. et al. Conformational and biological characterization of human parathyroid hormone hPTH(1-34) analogs containing beta-amino acid residues in positions 17-19. *Biopolymers* 70, 534-547 (2003).
19. Shimizu, M., Potts, J. T. & Gardella, T. J. Minimization of parathyroid hormone—Novel amino-terminal parathyroid hormone fragments with enhanced potency in activating the type-1 parathyroid hormone receptor. *J. Biol. Chem.* 275, 21836-21843 (2000).
20. Serada, M. et al. The role of the liver and kidneys in the pharmacokinetics of subcutaneously administered teriparatide acetate in rats. *Xenobiotica* 42, 398-407 (2012).
21. Maeda, A., et al. Critical role of parathyroid hormone (PTH) receptor-1 phosphorylation in regulating acute responses to PTH. *Proc. Natl. Acad. Sci. U.S.A.* 110, 5864-5869 (2013).
22. Lagerstrom, M. C. & Schioth, H. B. Structural diversity of G protein-coupled receptors and significance for drug discovery. *Nat. Rev. Drug Discovery* 7, 339-357 (2008).
23. Pal, K., Melcher, K. & Xu, H. E. Structure and mechanism for recognition of peptide hormones by Class B G-protein-coupled receptors. *Acta Pharmacol. Sin.* 33, 300-311 (2012).
24. Parthier, C., Reedtz-Runge, S., Rudolph, R. & Stubbs, M. T. Passing the baton in class B GPCRs: peptide hormone activation via helix induction? *Trends Biochem. Sci.* 34, 303-310 (2009).
25. Koth, C. M. et al. Molecular basis for negative regulation of the glucagon receptor. *Proc. Natl. Acad. Sci. U.S.A.* 109, 14393-14398 (2012).
26. Rasmussen, S. G. F. et al. Crystal structure of the β$_2$ adrenergic receptor-Gs protein complex. *Nature* 477, 549-U311 (2011).
27. Uzawa, T., Hori, M., Ejiri, S. & Ozawa, H. Comparison of the Effects of Intermittent and Continuous Administration of Human Parathyroid Hormone (1-34) on Rat Bone. *Bone* 16, 477-484 (1995).
28. Qin, L., Raggatt, L. J. & Partridge, N.C. Parathyroid hormone: a double-edged sword for bone metabolism. *Trends in Endocrinology and Metabolism* 15, 60-65 (2004).
29. Kostenuik, P. J. et al. Infrequent delivery of a long-acting PTH-Fc fusion protein has potent anabolic effects on cortical and cancellous bone. *Journal of Bone and Mineral Research* 22, 1534-1547 (2007).
30. Horne, W. S., Boersma, M. D., Windsor, M. A. & Gellman, S. H. Sequence-based design of α/β-peptide foldamers that mimic BH3 domains. *Angew. Chem. Int. Ed.* 47, 2853-2856 (2008).
31. King, D. S., Fields, C. G., and Fields, G. B. A cleavage method which minimizes side reactions following FMOC solid-phase peptide-synthesis, *International Journal of Peptide and Protein Research* 36, 255-266 (1990).
32. Horne, W. S. et al. Structural and biological mimicry of protein surface recognition by α/β-peptide foldamers. *Proc. Natl. Acad. Sci. U.S.A.* 106, 14751-14756 (2009).
33. Gill, S. C. & Vonhippel, P. H. Calculation of protein extinction coefficients from amino-acid sequence data. *Analytical Biochemistry* 182, 319-326 (1989)
34. Gardella, T. J., Wilson, A. K., Keutmann, H. T., Oberstein, R., Potts, J. T., Kronenberg, H. M., and Nussbaum, S. R. Analysis of Parathyroid Hormone's Principal Receptor-binding Region by Site-directed Mutagenesis and Analog, *Endocrinology* 132, 2024-2030 (1993).

What is claimed is:

1. An isolated, unnatural peptide analogue comprising: PTH, a parathyroid hormone receptor (PTHR-1, PTHR-2) agonist-effective fragment of PTH, a parathyroid hormone related protein (PTHrP), a PTHR-1 or PTHR-2 agonist-effective fragment of PTHrP, M-PTH, a PTHR-1 or PTHR-2 agonist-effective fragment of M-PTH, abaloparatide (BA058), or a PTHR-1 or PTHR-2 agonist-effective fragment of abaloparatide, in which at least one naturally occurring (L)-α-amino acid residue at position 6 or 7 from the N-terminus is replaced with a β-amino acid residue; and salts thereof.

2. The peptide analogue of claim 1, wherein the at least one naturally occurring (L)-α-amino acid residue at position 6 or 7 from the N-terminus is replaced with a $\beta^2$-amino acid residue.

3. The peptide analogue of claim 2, wherein the at least one naturally occurring (L)-α-amino acid residue at 6 or 7 from the N-terminus is replaced with a $\beta^2$-amino acid residue having a side-chain identical to the (L)-α-amino acid residue replaced.

4. The peptide analogue of claim 1, wherein the at least one naturally occurring (L)-α-amino acid residue at 6 or 7 from the N-terminus is replaced with a $\beta^3$-amino acid residue.

5. The peptide analogue of claim 4, wherein the at least one naturally occurring (L)-α-amino acid residue at 6 or 7 from the N-terminus is replaced with a $\beta^3$-amino acid residue having a side-chain identical to the (L)-α-amino acid residue replaced.

6. The peptide analogue of claim 1, wherein the at least one naturally occurring (L)-α-amino acid residue at 6 or 7 from the N-terminus is replaced with a (D)-α-amino acid.

7. The peptide analogue of claim 6, wherein the at least one naturally occurring (L)-α-amino acid residue at 6 or 7 from the N-terminus is replaced with a (D)-α-amino acid residue having a side-chain identical to the (L)-α-amino acid residue replaced.

8. The peptide analogue of claim 1, selected from the group consisting of

```
                                              (SEQ ID NO: 8)
SVSEIQLMHNLGKHLNSMERVEWLRKKLQDVHNF, (SEQ ID NO: 14)
SVSEIQLMHNLGKHLNSMERVEWLRKKLQDVHNF,
and
                                              (SEQ ID NO: 15)
SVSEIQLMHNLGKHLNSMERVEWLRKKLQDVHNF;
``` wherein
L=(R*) β² leucine;
Q=(S*) β² glutamine;
V=(R*) β² valine; and
S=β² serine.

9. The peptide analogue of claim 1, in which at least one additional naturally occurring (L)-α-amino acid residue at position 1 or 2 from the N-terminus is replaced with a β-amino acid residue or a (D)-α-amino acid.

10. An isolated, unnatural peptide analogue selected from the group consisting of:
PTH, a parathyroid hormone receptor (PTHR-1, PTHR-2) agonist-effective fragment of PTH, a parathyroid hormone related protein (PTHrP), a PTHR-1 agonist-effective fragment of PTHrP, a PTHR-2 agonist-effective fragment of PTHrP, M-PTH, a PTHR-1 agonist-effective fragment of M-PTH, a PTHR-2 agonist-effective fragment of M-PTH, abaloparatide (BA058), a PTHR-1 agonist-effective fragment of abaloparatide, and a PTHR-2 agonist-effective fragment of abaloparatide, in which at least one naturally occurring (L)-α-amino acid residue at position 6 or 7 from the N-terminus is replaced with a β-amino acid residue; and
salts thereof.

11. The peptide analogue of claim 10, wherein the at least one naturally occurring (L)-α-amino acid residue at position 6 or 7 from the N-terminus is replaced with a β²-amino acid residue.

12. The peptide analogue of claim 11, wherein the at least one naturally occurring (L)-α-amino acid residue at position 6 or 7 from the N-terminus is replaced with a β²-amino acid residue having a side-chain identical to the (L)-α-amino acid residue replaced.

13. The peptide analogue of claim 10, wherein the at least one naturally occurring (L)-α-amino acid residue at position 6 or 7 from the N-terminus is replaced with a β³-amino acid residue.

14. The peptide analogue of claim 13, wherein the at least one naturally occurring (L)-α-amino acid residue at position 6 or 7 from the N-terminus is replaced with a β³-amino acid residue having a side-chain identical to the (L)-α-amino acid residue replaced.

15. The peptide analogue of claim 10, wherein the at least one naturally occurring (L)-α-amino acid residue at position 6 or 7 from the N-terminus is replaced with a (D)-α-amino acid.

16. The peptide analogue of claim 15, wherein the at least one naturally occurring (L)-α-amino acid residue at position 6 or 7 from the N-terminus is replaced with a (D)-α-amino acid residue having a side-chain identical to the (L)-α-amino acid residue replaced.

17. The peptide analogue of claim 10, selected from the group consisting of

```
                                    (SEQ ID NO: 8)
SVSEIQLMHNLGKHLNSMERVEWLRKKLQDVHNF, (SEQ ID NO: 14)
SVSEIQLMHNLGKHLNSMERVEWLRKKLQDVHNF,
and (SEQ ID NO: 15)
SVSEIQLMHNLGKHLNSMERVEWLRKKLQDVHNF;
``` wherein L=(R*) β² leucine;
Q=(S*) β² glutamine;
V=(R*) β² valine; and
S=β² serine.

18. The peptide analogue of claim 10, in which at least one additional naturally occurring (L)-α-amino acid residue at position 1 or 2 from the N-terminus is replaced with a β-amino acid residue or a (D)-α-amino acid.

19. A pharmaceutical composition for treating hypoparathyroidism, the composition comprising a parathyroid hormone receptor agonist-effective amount of PTH, a parathyroid hormone receptor (PTHR-1, PTHR-2) agonist-effective fragment of PTH, a parathyroid hormone related protein (PTHrP), a PTHR-1 agonist-effective fragment of PTHrP, a PTHR-2 agonist-effective fragment of PTHrP, M-PTH, a PTHR-1 agonist-effective fragment of M-PTH, a PTHR-2 agonist-effective fragment of M-PTH, abaloparatide (BA058), a PTHR-1 agonist-effective fragment of abaloparatide, and a PTHR-2 agonist-effective fragment of abaloparatide, in which at least one naturally occurring (L)-α-amino acid residue at position 6 or 7 from the N-terminus is replaced with a β-amino acid residue; and pharmaceutically suitable salts thereof, in combination with a pharmaceutically suitable carrier.

20. A method of treating hypoparathyroidism in a mammalian subject, including a human subject, the method comprising administering to the subject a parathyroid hormone receptor agonist-effective amount of a pharmaceutical composition as recited in claim 19.

\* \* \* \* \*